(12) United States Patent
Shi et al.

(10) Patent No.: US 9,238,093 B2
(45) Date of Patent: Jan. 19, 2016

(54) SURFACE IMPROVEMENT ON ELECTRIC DISCHARGE MACHINED TITANIUM ALLOY MINIATURE PARTS FOR IMPLANTABLE MEDICAL DEVICE

(75) Inventors: Alan Shi, Plymouth, MN (US); Bernard Q. Li, Plymouth, MN (US); Daniel D. Sorensen, Blaine, MN (US); Darren A. Janzig, Center City, MN (US)

(73) Assignee: Medtronic, Inc, Minneapolis, MN (US)

( * ) Notice: Subject to any disclaimer, the term of this patent is extended or adjusted under 35 U.S.C. 154(b) by 183 days.

(21) Appl. No.: 13/301,158

(22) Filed: Nov. 21, 2011

(65) Prior Publication Data
US 2013/0126474 A1    May 23, 2013

(51) Int. Cl.
| | | |
|---|---|---|
| C23F 1/18 | (2006.01) | |
| C23F 1/20 | (2006.01) | |
| C23F 1/26 | (2006.01) | |
| C23F 1/30 | (2006.01) | |
| A61L 31/02 | (2006.01) | |
| A61L 27/06 | (2006.01) | |
| A61L 27/50 | (2006.01) | |
| A61L 31/14 | (2006.01) | |
| B23H 7/02 | (2006.01) | |

(52) U.S. Cl.
CPC .............. *A61L 31/022* (2013.01); *A61L 27/06* (2013.01); *A61L 27/50* (2013.01); *A61L 31/14* (2013.01); *C23F 1/18* (2013.01); *C23F 1/20* (2013.01); *C23F 1/26* (2013.01); *C23F 1/30* (2013.01); *A61L 2400/18* (2013.01); *B23H 7/02* (2013.01)

(58) Field of Classification Search
None
See application file for complete search history.

(56) References Cited

U.S. PATENT DOCUMENTS

| | | | |
|---|---|---|---|
| 3,048,503 A * | 8/1962 | Foote et al. ................. | 134/9 |
| 4,353,780 A | 10/1982 | Fishter et al. | |
| 5,330,441 A * | 7/1994 | Prasad et al. .................. | 606/222 |
| 5,660,640 A * | 8/1997 | Laube ................. | 134/1 |
| 6,309,556 B1 * | 10/2001 | Joyce et al. ................... | 216/100 |
| 7,682,937 B2 | 3/2010 | Evertsen et al. | |
| 2003/0130736 A1* | 7/2003 | Raab ......................... | 623/16.11 |
| 2003/0221702 A1* | 12/2003 | Peebles ......................... | 134/1 |
| 2004/0134886 A1* | 7/2004 | Wagner et al. ................. | 216/89 |
| 2004/0167625 A1* | 8/2004 | Beyar et al. ................. | 623/11.11 |
| 2006/0210846 A1* | 9/2006 | Isozaki et al. ................... | 429/19 |
| 2006/0229733 A1* | 10/2006 | Steinemann et al. ........ | 623/23.5 |
| 2008/0221664 A1* | 9/2008 | Bales et al. ................. | 623/1.22 |
| 2009/0326674 A1* | 12/2009 | Liu et al. ..................... | 623/23.55 |
| 2011/0151671 A1* | 6/2011 | Barr et al. ..................... | 438/695 |
| 2011/0214785 A1* | 9/2011 | Buckman et al. ............ | 148/237 |
| 2012/0295446 A1* | 11/2012 | Prajapati et al. ............. | 438/745 |
| 2013/0092555 A1* | 4/2013 | Haluck et al. ................ | 205/661 |

FOREIGN PATENT DOCUMENTS

EP            2180083 A1 *   4/2010
WO     WO 2009/149197     12/2009

* cited by examiner

*Primary Examiner* — Anita Alanko

(57) ABSTRACT

The invention describes a process to remove a recast layer and/or burrs from machining processes to provide a surface of a titanium medical device without dissipation of copper or zinc from the surface of the medical device.

15 Claims, 36 Drawing Sheets

SURFACE IMPROVEMENT ON ELECTRIC DISCHARGE MACHINED TITANIUM ALLOY MINIATURE PARTS FOR IMPLANTABLE MEDICAL DEVICE

CROSS REFERENCE TO RELATED APPLICATIONS

None

FIELD OF THE INVENTION

The invention relates generally to a method to remove a copper/zinc containing recast layer, recast spatter or burrs from a machined surface.

BACKGROUND OF THE INVENTION

Implantable medical devices (IMDs) are used to produce therapeutic results in a patient and for monitoring physiologic parameters of a patient. Examples of IMDs include implantable drug infusion pumps, implantable neurostimulators, implantable cardioverter defibrillators, implantable cardiac pacemakers, and cochlear implants. Most of these IMDs often provide an electrical output, contain electrical circuitry, and or contain metallic components such as springs, to perform their intended functions. These devices are typically powered by a battery contained within the housing of the implantable medical device.

Commercially pure (CP) Ti and Ti alloys are an important category of materials for construction of implantable medical device (IMD). In some cases, CP Ti does not meet required design requirements. Thus far, suitable Ti alloys that can be used in IMDs include Grade 5 Ti (Ti-6Al-4V), Ti15Mo, Ti30Ta, Ti45Nb, TNTZ, and TNCZ in view of their purity and non-release of unwanted metal ions such as copper (Cu) and/or zinc (Zn). Machining of the parts often causes undesired burrs to form on the machined surface and/or other unwanted trace metals may remain, such as Cu and/or Zn.

Therefore, a need exists for methods and products that overcome one or more of the current disadvantages noted above.

BRIEF SUMMARY OF THE INVENTION

As IMDs are becoming increasingly compact, sophisticated, and provide more function, miniaturization of parts is becoming a necessity. One viable and economic way to make miniature Ti alloy parts is by electrical discharging machining (EDM). EDM processes can meet the tight dimensional tolerance that miniature parts often require. However, EDM processes can leave a re-cast layer and/or splatter on the machined part's surface composed of copper and zinc. Copper may have toxicity issues and the re-cast layer may cause wear debris if there is mechanical motion while is use.

Additionally, the EDM process can also cause the machined part to have burrs on the machined surface of the part.

Additional methods to machine intricate parts include laser cutting or by water jet cutting. These two methods can also cause formation of burrs or splatter on the surface of the machined part.

The present invention provides a method to remove a recast layer, and/or splatter material composed of copper and zinc produced by an EDM process on titanium based IMD components. Similarly, removal of burrs from the IMD surface can be accomplished as well by the processes described herein. For example, use of an aqueous solution of 1-3 volume percent of hydrofluoric acid (HF) in 20-40 volume percent nitric acid (HNO$_3$) for a period of time removes the recast layer, burrs and/or splatter material from EDM machined parts. Typically, the machined part is placed into the acidic solution at a temperature of from about 10° C. to about 60° C. for a period of about 30 seconds to about 10 minutes with or without sonication. The IMD machined part is removed from the acid bath and rinsed with water to provide an IMD devoid of a recast surface layer, burrs and/or splatter material from an EDM process.

The acid treatment described above can also be applied to surfaces that have been machined by laser cutting or water jet cutting where burrs and/or splatter are formed on the machined surface. Use of the acid treatment described herein removes/dissolves the burrs and splatter providing a surface free of such burrs and/or splatter.

In one aspect, the acid treatment described above can provide a treated surface substantially devoid of etch pits.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 8(*b*) provides a magnified SEM image of FIG. 8(*a*) showing top surface of valve retainer 30, vertical drug flow channel 20, horizontal WEDM plane 40 with recast layer (roughened surface) and horizontal surface 50 with recast splatter. The arrows mark the horizontal WEDM horizontal plane 40.

FIG. 8(*c*) is an SEM of increased magnification of FIG. 8(*a*) showing horizontal WEDM plane 40 with recast layer (flakey roughened surface) and horizontal surface 50 with recast splatter 60.

FIG. 8(*d*) is an SEM of FIG. 8(*a*) showing horizontal WEDM plane 40 with recast layer in the form of a roughened surface and/or flakes.

FIGS. 8(*e*) and 8(*f*) are SEMs at increased magnifications of the surface morphology of horizontal surface 50 with recast splatter 60.

FIGS. 8(*g*) and 8(*h*) are SEMS at increased magnifications of the surface morphology of top surface of valve retainer 30.

FIGS. 9(*b*), (*c*), and (*d*) are successive higher magnification SEM images of FIG. 8(*a*) after 1 minute of etching with 2 vol % HF in 30 vol % HNO$_3$ acid at room temperature with sonication (40 KHz), followed by rinsing and drying. The arrows mark the horizontal WEDM horizontal plane 40.

FIG. 9(*b*) provides a magnified SEM image of FIG. 9(*a*) showing top surface of valve retainer 30, vertical drug flow channel 20, horizontal WEDM plane with recast layer (roughened surface) removed and horizontal surface 50 with recast splatter removed after 1 minute of etching with 2 vol % HF in 30 vol % HNO$_3$ acid at room temperature with sonication (40 KHz), followed by rinsing and drying.

FIG. 9(*c*) is an SEM of increased magnification of FIG. 9(*a*) showing horizontal WEDM plane 40 with recast layer (flakey roughened surface) removed and horizontal surface 50 with recast splatter 60 removed after 1 minute of etching with 2 vol % HF in 30 vol % HNO$_3$ acid at room temperature with sonication (40 KHz), followed by rinsing and drying.

FIG. 9(*d*) is an SEM of FIG. 9(*a*) showing horizontal WEDM plane 40 without the recast layer after 1 minute of etching with 2 vol % HF in 30 vol % HNO$_3$ acid at room temperature with sonication (40 KHz), followed by rinsing and drying.

FIGS. 9(*e*) and 9(*f*) are SEMs at increased magnifications of the surface morphology of horizontal surface 50 without recast splatter 60 after 1 minute of etching with 2 vol % HF in 30 vol % HNO$_3$ acid at room temperature with sonication (40 KHz), followed by rinsing and drying.

FIGS. 9(*g*) and 9(*h*) are SEMS at increased magnifications of the surface morphology of top surface of valve retainer 30 after 1 minute of etching with 2 vol % HF in 30 vol % HNO$_3$ acid at room temperature with sonication (40 KHz), followed by rinsing and drying.

FIGS. 10(*b*), (*c*), and (*d*) are successive higher magnification SEM images of FIG. 8(*a*) after 2 minutes of etching with 2 vol % HF in 30 vol % HNO$_3$ acid at room temperature with sonication (40 KHz), followed by rinsing and drying.

FIG. 10(*b*) provides a magnified SEM image of FIG. 8(*a*) showing top surface of valve retainer 30, vertical drug flow channel 20, horizontal WEDM plane without recast layer (roughened surface) and horizontal surface 50 without recast splatter after 2 minutes of etching with 2 vol % HF in 30 vol % HNO$_3$ acid at room temperature with sonication (40 KHz), followed by rinsing and drying. The arrows mark the horizontal WEDM horizontal plane 40.

FIG. 10(*c*) is an SEM of increased magnification of FIG. 10(*a*) showing horizontal WEDM plane 40 without recast layer and horizontal surface 50 without recast splatter 60 after 2 minutes of etching with 2 vol % HF in 30 vol % HNO$_3$ acid at room temperature with sonication (40 KHz), followed by rinsing and drying. Etch pits 70 in the titanium surface are now noted.

FIG. 10(*d*) is an SEM of FIG. 10(*a*) showing horizontal WEDM plane 40 with etch pits 70 after 2 minutes of etching with 2 vol % HF in 30 vol % HNO$_3$ acid at room temperature with sonication (40 KHz), followed by rinsing and drying.

FIGS. 10(*e*) and 10(*f*) are SEMs at increased magnifications of the surface morphology of horizontal surface 50 with etch pits 70 after 2 minutes of etching with 2 vol % HF in 30 vol % HNO$_3$ acid at room temperature with sonication (40 KHz), followed by rinsing and drying.

FIGS. 10(*g*) and 10(*h*) are SEMS at increased magnifications of the surface morphology of top surface of valve retainer 30 after 2 minutes of etching with 2 vol % HF in 30 vol % HNO$_3$ acid at room temperature with sonication (40 KHz), followed by rinsing and drying.

FIGS. 11(*b*), (*c*), and (*d*) are successive higher magnification SEM images of FIG. 11(*a*) after 3 minutes of etching with 2 vol % HF in 30 vol % HNO$_3$ acid at room temperature with sonication (40 KHz), followed by rinsing and drying.

FIG. 11(*b*) provides a magnified SEM image of FIG. 8(*a*) showing top surface of valve retainer 30, vertical drug flow channel 20, horizontal WEDM plane without recast layer (roughened surface) and horizontal surface 50 without recast splatter 60 after 3 minutes of etching with 2 vol % HF in 30 vol % HNO$_3$ acid at room temperature with sonication (40 KHz), followed by rinsing and drying. Etch pits 70 were noted on the titanium surface. The arrows mark the horizontal WEDM horizontal plane 40.

FIG. 11(*c*) is an SEM of increased magnification of FIG. 11(*a*) showing horizontal WEDM plane 40 without recast layer and horizontal surface 50 without recast splatter 60 after 3 minutes of etching with 2 vol % HF in 30 vol % HNO$_3$ acid at room temperature with sonication (40 KHz), followed by rinsing and drying. Etch pits 70 in the titanium surface were noted.

FIG. 12(b) provides a magnified SEM image of FIG. 8(a) showing top surface of valve retainer 30, vertical drug flow channel 20, horizontal WEDM plane without recast layer (roughened surface) and horizontal surface 50 without recast splatter 60 after 4 minutes of etching with 2 vol % HF in 30 vol % HNO$_3$ acid at room temperature with sonication (40 KHz), followed by rinsing and drying. Etch pits 70 were noted on the titanium surface. The arrows mark the horizontal WEDM horizontal plane 40.

FIG. 13(b) provides a magnified SEM image of FIG. 8(a) showing top surface of valve retainer 30, vertical drug flow channel 20, horizontal WEDM plane without recast layer (roughened surface) and horizontal surface 50 without recast splatter 60 after 5 minutes of etching with 2 vol % HF in 30 vol % HNO$_3$ acid at room temperature with sonication (40 KHz), followed by rinsing and drying. Etch pits 70 were noted on the titanium surface. The arrows mark the horizontal WEDM horizontal plane 40.

DETAILED DESCRIPTION

Figure 1A:
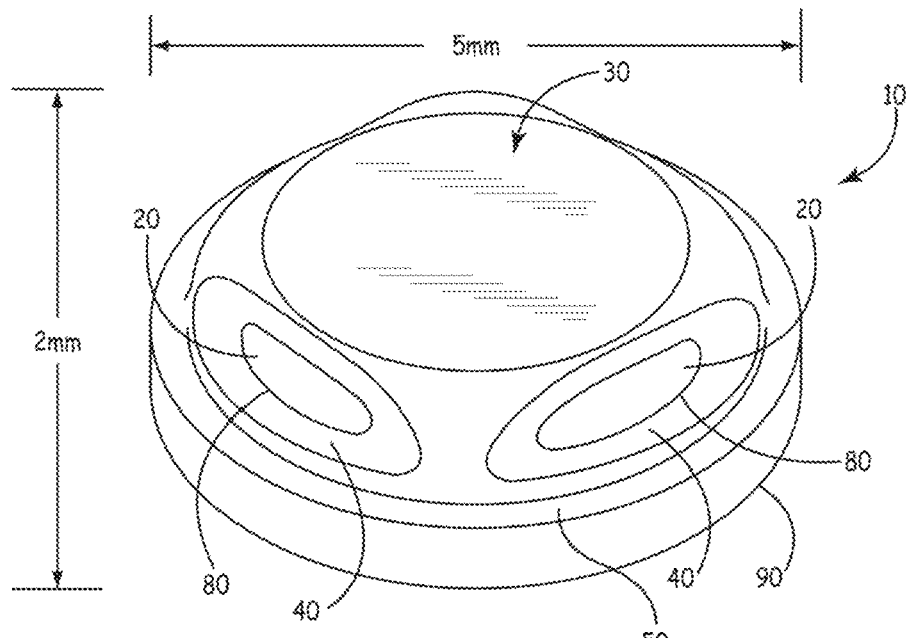
FIG. 1(a) is a perspective representation of a medical device valve retainer 10 that has been cut by a wire electrical discharge machining (WEDM) process. The view provides vertical drug flow channels 20 formed by the WEDM process, a top surface 30 of valve retainer 10, horizontal WEDM plane 40, horizontal surface 50 below horizontal WEDM plane 40 and inner wall 80 of horizontal WEDM plane 40. The dimensions noted in FIG. 1(a) are not intended to be limiting but only representative for the width (approximately 5 mm) and the height (approximately 2 mm) of the valve retainer 10.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The phrase "recast layer" is intended to refer to a layer that is formed on a surface during EDM processing, such as WEDM. During the EDM process, bronze is used, which deposits a layer of copper and zinc, known as the "recast layer" onto the machined surface. Prior to the present invention, it was not appreciated that recast material should be removed from a machined surface and was allowed to remain on the machined surface.

The term "splatter" is intended to refer to material that is randomly deposited on an EDM processed part. The components of the random deposits comprise copper and zinc and originate from the bronze utilized in the EDM process.

The term "burr" is intended to refer to a deformation of metal where a raised portion is formed on a metal part which has been machined.

In one embodiment, a surface modified alloy is provided that has been treated to remove a recast layer, splatter, or burrs from the surface of the alloy. In one aspect, such treatment removes copper or zinc from the recast layer of a machined alloy. Such treated alloys can be used for various implantable medical devices (IMDs) including, but not limited to, implantable drug infusion pumps, implantable neurostimulators, implantable cardioverter defibrillators, implantable cardiac pacemakers, electrical leads, conductor coils, connector blocks, implantable stents, bellows and cochlear implants.

Suitable materials useful to prepare IMDs include titanium, molybdenum, niobium, zirconium, tantalum, aluminum, vanadium or mixtures thereof.

Commercially pure (CP) Ti and Ti alloys are an important category of materials for construction of implantable medical devices (IMDs). Suitable Ti alloys that can be used in IMDs include Grade 5 Ti (Ti-6Al-4V), Ti15Mo, Ti30Ta, Ti45Nb, TNTZ, and TNCZ.

In one aspect, the alloy part suitable for an IMD is machined by an EDM process, such as WEDM, and then subsequently treated to remove a recast layer, burrs and/or splatter as a result of the EDM process.

Electrical discharging machining (EDM) also known as spark machining, spark eroding, burning, die sinking or wire erosion, refers to a manufacturing process whereby a desired shape is obtained using electrical discharges (sparks). Material is removed from the work piece by a series of rapidly recurring current discharges between two electrodes, separated by a dielectric liquid and subject to an electric voltage. One of the electrodes is called the tool-electrode, or simply the tool or electrode, while the other is called the work piece-electrode, or work piece.

In wire electrical discharge machining (WEDM), also known as wire-cut EDM and wire cutting, a thin single-strand metal wire, usually brass, is fed through the work piece and submerged in a tank of dielectric fluid, typically deionized water. The brass used in the process is the source of the contaminating copper and/or zinc. The brass material forms the recast layer on the surface that was cut as well as splatter from brass being cast off from the process.

The wire, which is fed from a spool, is held between upper and lower diamond guides. The guides, usually computer numeric controlled, move in the x-y plane. On most machines, the upper guide can also move independently in the z-u-v axis, giving rise to the ability to cut tapered and transitioning shapes. The upper guide can control axis movements in x-y-u-v-i-j-k-l-directions. This allows the wire-cut EDM to be programmed to cut very intricate and delicate shapes.

In one embodiment, the present invention provides a method to remove a recast layer, burrs and/or splatter material produced by an EDM process on the surface of titanium based IMD components. Use of an aqueous solution of 1-3 volume percent of hydrofluoric acid (HF) in 20-40 volume percent nitric acid ($HNO_3$) for a period of time removes the recast layer, burrs and/or splatter material from EDM machined parts. Typically, the machined part is placed into the acidic solution at a temperature of from about 10° C. to about 60° C. for a period of about 30 seconds to about 10 minutes with or without ultrasonication. The IMD part is removed from the acid bath and rinsed with a solvent, such as water, to provide an IMD devoid of a recast surface layer, burrs or splatter material from the EDM process.

The treatment solution includes an aqueous solution of 1 to about 3 volume percent of hydrofluoric acid, in particular, about 1 to about 2 volume percent and particularly about 2 volume percent. The treatment solution also includes from about 20 to about 40 volume percent of nitric acid, more particularly about 30 volume percent.

The treatment solution can, optionally, contain other additives such as solvents, surfactants, additional acids or mixtures thereof. Suitable solvents include lower chain alcohols. Suitable acids include hydrochloric acid or citric acid.

The process is generally performed at a temperature range of from about 10° C. to about 60° C., more particularly from about 15° C. to about 30° C. and in particular, at ambient conditions.

Additionally, the process can be performed with the work piece being immersed in the treatment solution while being sonicated. Sonication can be effected at about 40 KHz.

The acid treatment process is conducted over a period of time from about 30 seconds to about 10 minutes, more particularly for about 5 minutes and most particularly from about 30 seconds to about 180 seconds.

In one aspect, the acid treatment provides a surface wherein the recast layer is removed, the recast splatter is removed and/or burr(s) are removed substantially without pitting of the underlying part surface.

The phrase "substantially without pitting" refers to a surface, when observed by SEM, provides a surface where pitting is substantially absent from the treated surface. Generally this is accomplished over a treatment period of from about 30 seconds to about 2 minutes with a treatment solution of about 2 vol % HF in 30 vol % $HNO_3$ at room temperature with sonication (40 KHz).

After the acid treatment of the machined part is complete, the treated machined part is generally rinsed. The rinse solution can be aqueous or an aqueous alcoholic solution.

As a result of the acid treatment, the recast layer, splatter and/or burrs are preferentially removed from the surface of the work piece. Generally, the removal depth of the recast layer, splatter and/or burrs from the surface is about 1 to about 100 microns, more particularly from about 10 to 100 microns, and even more particularly from about 20 to about 50 microns.

Not to be limited by theory, it is believed that the chemical composition and/or morphology of the recast layer, splatter and/or burr is more susceptible to etching removal than the underlying titanium surface. This selective removal may also be due to voids, pits, grooves, incomplete coverage, etc. of the recast layer, splatter and/or burrs on the titanium surface. It should be understood that partial or insubstantial removal of the titanium surface can also occur, however, to a much less diminished degree than the recast layer, splatter and/or burrs. For example, the etching of the titanium base material can be seen in FIGS. 10($a$) through 10($h$) and FIGS. 13($a$) through 13($h$) where etch pits are noted in the titanium base material. This is described in more detail below.

In one aspect, a quadratic relationship has been established between unwanted material removal (such as a recast layer, burrs, and/or splatter) and the processing time of the acid treatment. This can be described by the equation: $L=0.000146+0.000363\,T+0.000179\,T^2$, where L is material removal in inches and T is time in minutes.

In another embodiment, the process parameters are also useful to treat laser cut or water jet cut machined parts. Use of laser cutting or water jet cutting often results in "burrs" on the machined part, especially in miniaturized parts.

Laser jet machining refers to technology that uses a laser to cut materials. Laser cutting works by directing the output of a high-power laser, by computer, upon the material to be cut. The material then either melts, burns, vaporizes away, or is blown away by a jet of gas, leaving an edge with a high-quality surface finish. A laser microjet is a water-jet guided laser in which a pulsed laser beam is coupled into a low-pressure water jet. This is used to perform laser cutting functions while using the water jet to guide the laser beam, much like an optical fiber, through total internal reflection. The advantages of this are that the water also removes debris and cools the material. Additional advantages over traditional "dry" laser cutting are high dicing speeds, parallel kerf and omnidirectional cutting.

Water jet machining refers to a tool capable of slicing into metal using a jet of water at high velocity and pressure, or a mixture of water and an abrasive substance.

Both water jet machining as well as laser jet machining often produce deformities on the work piece surface in the form of burrs.

The following paragraphs enumerated consecutively from 1 through 38 provide for various aspects of the present invention. In one embodiment, in a first paragraph (1), the present invention provides a process comprising the steps:

providing a metallic electric discharge machined (EDM) part with a recast layer or splatter from the EDM machining;

contacting the EDM part with the recast layer or splatter with a treatment solution comprising an aqueous solution of 1-3 volume percent hydrofluoric acid and 20-40 volume percent nitric acid to remove the recast layer or splatter, providing a treated EDM part devoid of a recast layer or splatter.

2. The process of paragraph 1, further comprising the step: rinsing the treated EDM part with a rinse solvent to provide a finished machined part.

3. The process of either of paragraphs 1 or 2, wherein the treatment solution is maintained at a temperature between about 10° C. and 60° C.

4. The process of paragraph 1, wherein the treatment solution is maintained at ambient temperature.

5. The process of any of paragraphs 1 through 4, wherein the EDM part is contacted with the treatment solution for a period of about 30 seconds to about 10 minutes.

6. The process of paragraph 5, wherein the period of time is from about 30 to about 180 seconds.

7. The process of any of paragraphs 1 through 6, wherein the contacting step further includes sonication.

8. The process of paragraph 7, wherein the sonication is conducted at 40 KHz.

9. The process of any of paragraphs 2 through 8, wherein the rinse solvent is water, an alcohol, or an aqueous alcoholic solution.

10. The process of paragraph 9, wherein the rinse solvent is water.

11. The process of any of paragraphs 1 through 10, wherein the treatment solution consists essentially of hydrofluoric acid, nitric acid and water.

12. The process of any of paragraphs 1 through 10, wherein the treatment solution further comprises hydrochloric acid, sulfuric acid, citric acid, an alcohol or mixtures thereof.

13. The process of any of paragraphs 1 through 12, wherein the metallic EDM machined part comprises titanium, molybdenum, niobium, zirconium, tantalum, aluminum, vanadium or mixtures thereof.

14. The process of paragraph 13, wherein the metal is a grade 2 to a grade 5 titanium.

15. The process of paragraph 13, wherein the metal is a titanium alloy.

16. The process of any of paragraphs 1 through 15, wherein the hydrofluoric acid is present at a concentration of 2 volume percent.

17. The process of any of paragraphs 1 through 16, wherein the nitric acid is present at a concentration of 30 volume percent.

18. The process of any of paragraphs 1 through 17, wherein a quadratic relationship is established between recast layer or splatter removal and processing time, wherein $L=0.000146+0.000363\,T+0.000179\,T^2$, where L is the recast layer or splatter layer in inches and T is time in minutes.

19. A process comprising the steps:

providing a machined part with a burr or splatter from machining;

contacting the machined part with a treatment solution comprising an aqueous solution of 1-3 volume percent hydrofluoric acid and 20-40 volume percent nitric acid to remove the burr or splatter, providing a treated machined part devoid of a recast layer or splatter.

20. The process of paragraph 19, further comprising the step:

rinsing the treated machined part with a rinse solvent to provide a finished machined part.

21. The process of either of paragraphs 19 or 20, wherein the treatment solution is maintained at a temperature between about 10° C. and 60° C.

22. The process of paragraph 19, wherein the treatment solution is maintained at ambient temperature.

23. The process of any of paragraphs 19 through 22, wherein the machined part is contacted with the treatment solution for a period of about 30 seconds to about 10 minutes.

24. The process of paragraph 23, wherein the period of time is from about 30 to about 180 seconds.

25. The process of any of paragraphs 19 through 25, wherein the contacting step further includes sonication.

26. The process of paragraph 25, wherein the sonication is conducted at 40 KHz.

27. The process of any of paragraphs 21 through 26, wherein the rinse solvent is water, an alcohol, or an aqueous alcoholic solution.

28. The process of paragraph 27, wherein the rinse solvent is water.

29. The process of any of paragraphs 19 through 28, wherein the treatment solution consists essentially of hydrofluoric acid, nitric acid and water.

30. The process of any of paragraphs 19 through 28, wherein the treatment solution further comprises hydrochloric acid, sulfuric acid, citric acid, an alcohol or mixtures thereof 31. The process of any of paragraphs 19 through 30, wherein the metallic machined part comprises titanium, molybdenum, niobium, zirconium, tantalum, aluminum, vanadium or mixtures thereof.

32. The process of paragraph 31, wherein the metal is a grade 2 to a grade 5 titanium.

33. The process of paragraph 31, wherein the metal is a titanium alloy.

34. The process of any of paragraphs 19 through 33, wherein the hydrofluoric acid is present at a concentration of 2 volume percent.

35. The process of any of paragraphs 19 through 34, wherein the nitric acid is present at a concentration of 30 volume percent.

36. The process of any of paragraphs 19 through 35, wherein a quadratic relationship is established between burr or splatter removal and processing time, wherein $L = 0.000146 + 0.000363\,T + 0.000179\,T^2$, where L is a burr or splatter layer in inches and T is time in minutes.

37. The process of any of paragraphs 19 through 36, wherein the machining is by laser cutting or water jet cutting.

38. The process of any of paragraphs 1 through 37, wherein from about 10 to about 100 microns of the recast layer, recast splatter or burr surface is removed.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Examples

Figure 1B:
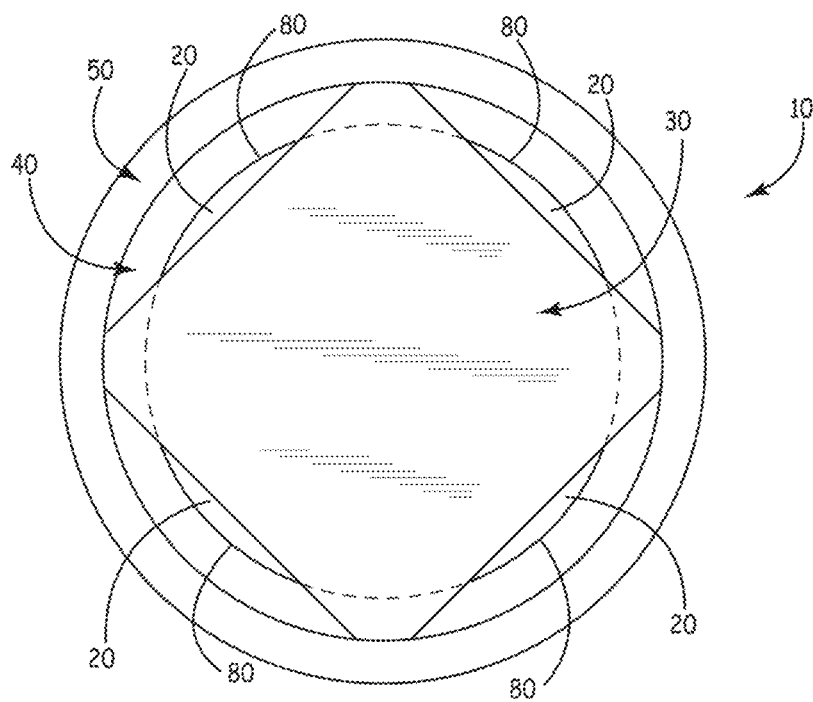
FIG. 1(b) is a top down perspective of FIG. 1(a).

Referring to FIGS. 1(a) and 1(b), the following data was based on valve retainers 10 used in an implantable infusion pump. The use of a valve retainer is exemplary and is not meant to be limiting. The processes described herein can be utilized on any surface where a recast layer or splatter is deposited onto a surface from an electric discharge process, such as wire electric discharge. The processes described herein can also be used for the removal of burrs as described above.

In FIGS. 1(a) and 1(b), the valve retainers 10 are made of commercially pure (CP) grade 2 titanium. The valve retainer 10 has four vertical drug flow channels 20 that permit a drug to flow downstream. The drug flow channels 20 are cut by a wire electric discharge machining (WEDM) process. The WEDM process results in a surface layer, the recast layer, of different morphology and chemistry than that of the commercially pure titanium valve retainer. When brass wire is used in the WEDM process, as in the following examples, the recast layer contains approximately 8 wt % of Cu and approximately 3 wt % of Zn with the balance being Ti on a weight percentage basis.

A valve retainer is a part of a drug delivery device. The valve retainer rests upon a spring which in turn rests upon a magnetic actuator which sits at the bottom portion 90 of valve retainer 10 thus creating a seal. Activation/deactivation of the actuator causes the spring to compress/decompress. When the actuator is activated, the spring is compressed and a liquid, such as aqueous drug solution, is released from a compartment of the drug delivery device adjacent to the magnetic actuator into valve retainer 10. The drug then flows out of the drug flow channels 20, generally into a catheter, to a treatment site. By activation/deactivation of the actuator, one can provide delivery of a drug over an extended period of time.

Materials and Methods

There are issues associated with WEDM machined surfaces. Because of the altered chemistry and morphology of the surface, the recast layer is expected to have degraded corrosion properties in comparison to the titanium. The recast layer may also contain small voids and cracks with high surface roughness, which may cause preferential protein aggregation onto the WEDM finished surfaces.

Additionally, the WEDM process results in splatter scattered in adjacent planes/surfaces about the work piece, such as horizontal surface 50 of valve retainer 10. The WEDM splatters in the form of particulates or aggregates that are loosely bonded to the substrate, and could become detached under physiological conditions.

Valve retainers 10 were used as shown in FIGS. 1(a) and 1(b). Samples were assigned individual identification numbers (IDs) from S1 to S15. Dimensional measurements were taken before and after chemical etch processing. Optical microscopy was performed before and after chemical etch processing. Scanning electron microscopy (SEM) and energy dispersive X-ray spectroscopy (EDS) were performed on the samples after chemical etching as well as on a control sample in an as-received condition.

The samples were chemically etched in 2 vol % HF in 30 vol % $HNO_3$ at room temperature with sonication (40 KHz) at 5 different time durations: 1 minute, 2 minutes, 3 minutes, 4 minutes, and 5 minutes, rinsed with deionized water and air dried. The samples were processed individually to maintain sample IDs. Each sample was prepared in triplicate.

Results

Optical Microscopy

Figure 2A:
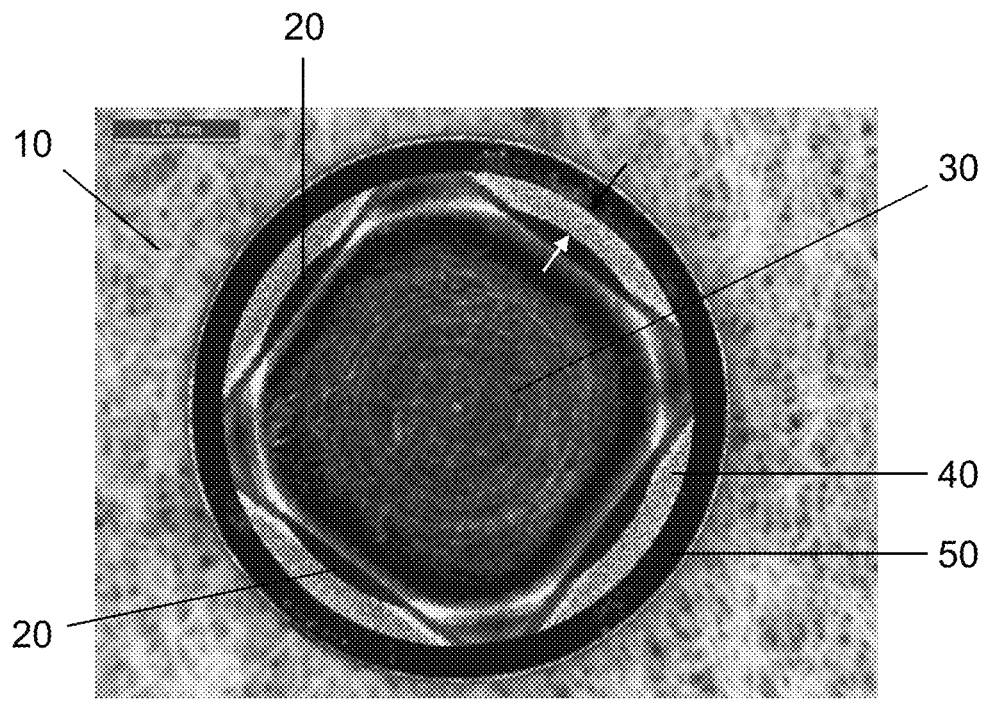
FIGS. 2(a) and 2(b) are optical images at two different magnifications of an as-received WEDM machined valve retainer 10. The arrows mark the horizontal WEDM horizontal plane 40. Vertical drug flow channels 20, which are perpendicular to horizontal WEDM plane 40 and top surface 30, were also prepared by an WEDM process.
Figure 2B:
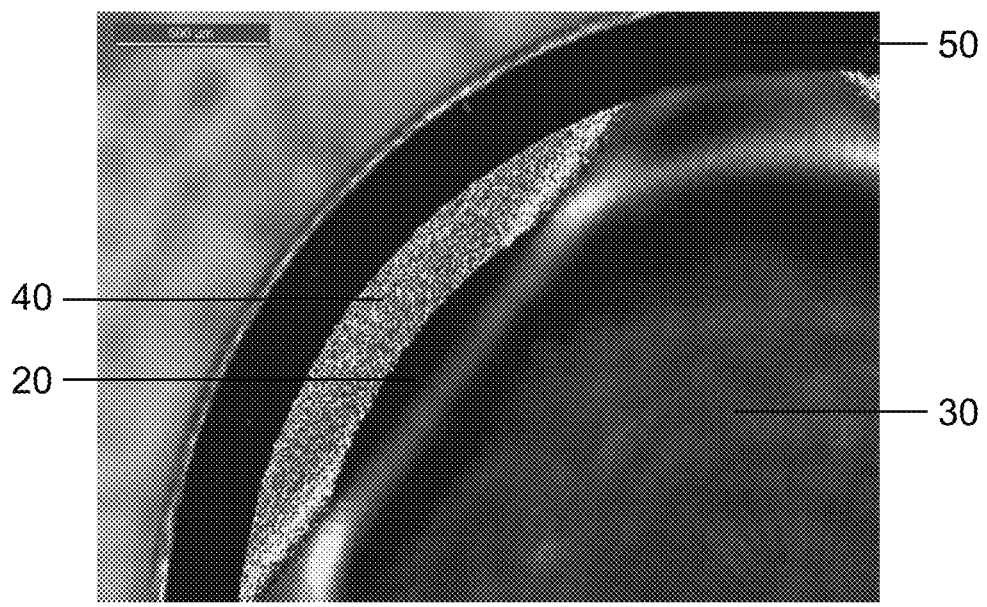

FIGS. 2(a) and 2(b) are optical images at two different magnifications of an as-received WEDM machined valve retainer 10. The two arrows indicate a portion of horizontal WEDM finished planes 40.

Figure 3A:
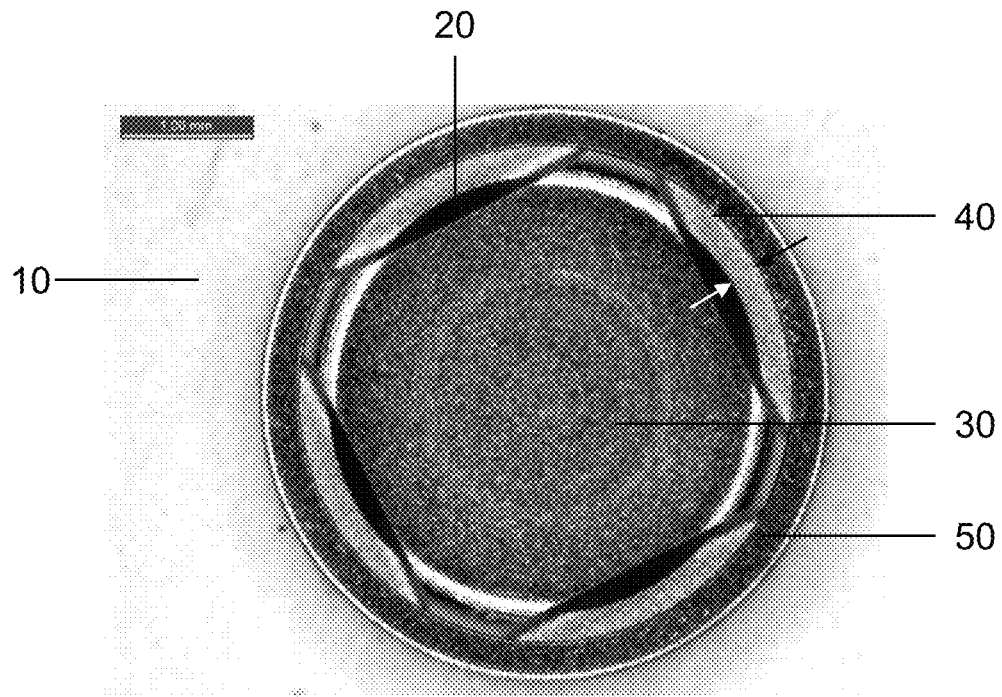
FIGS. 3(a) and 3(b) are optical images at two different magnifications of valve retainer 10 that was chemically etched for 1 minute in 2 vol % HF in 30 vol % HNO$_3$ at room temperature with sonication (40 KHz), followed by rinsing and drying. The arrows mark the horizontal WEDM horizontal plane 40.
Figure 3B:
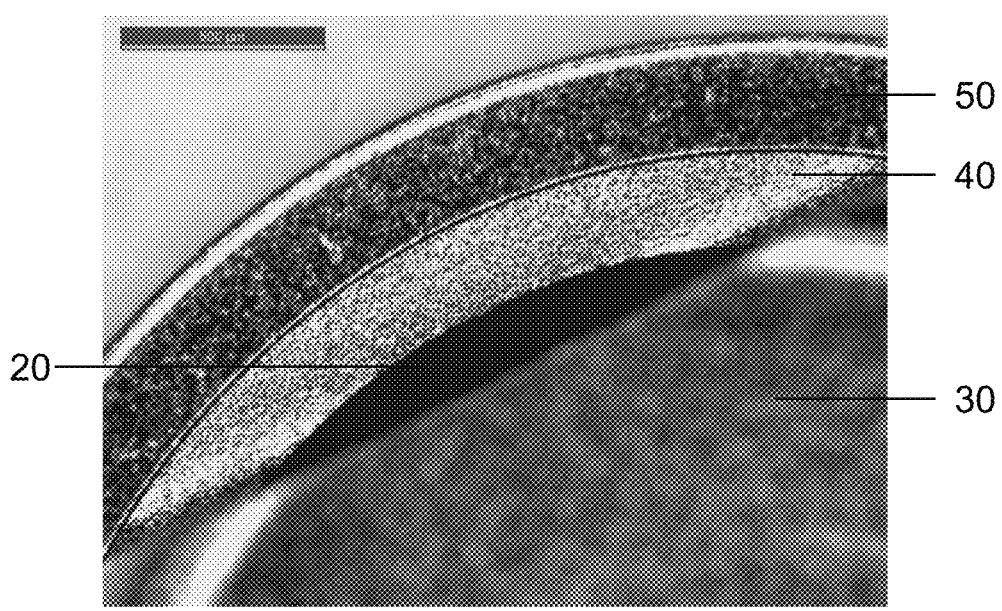

FIGS. 3(a) and 3(b) provide optical images of valve retainer 10 as exemplified in FIGS. 2(a) and 2(b), after 1 minute of etch treatment as described above. The arrows mark horizontal WEDM plane 40.

Figure 4A:
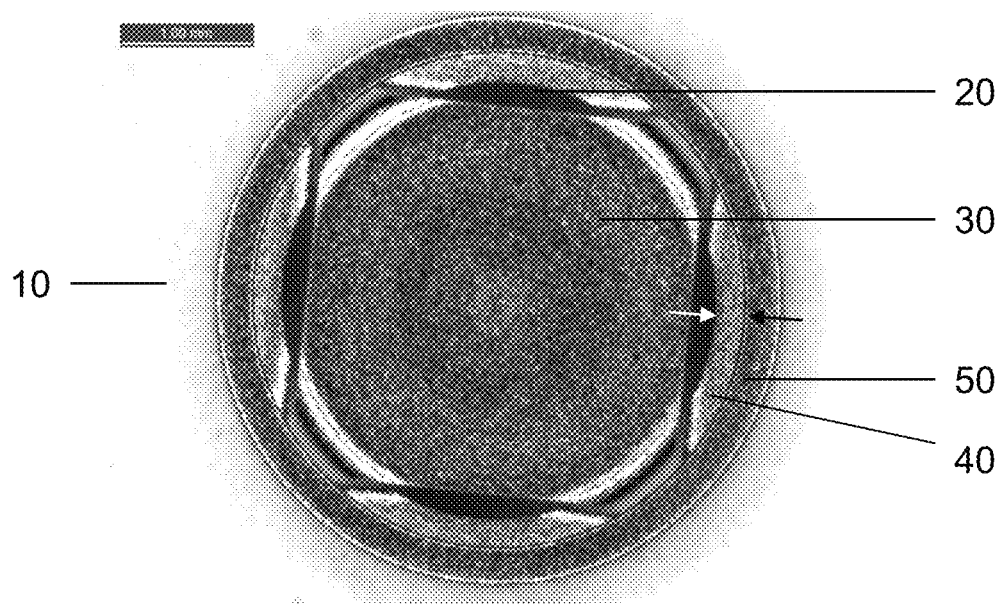
FIGS. 4(a) and 4(b) are optical images at two different magnifications of valve retainer 10 that was chemically etched for 2 minutes in 2 vol % HF in 30 vol % HNO$_3$ at room temperature with sonication (40 KHz), followed by rinsing and drying. The arrows mark the horizontal WEDM horizontal plane 40.
Figure 4B:
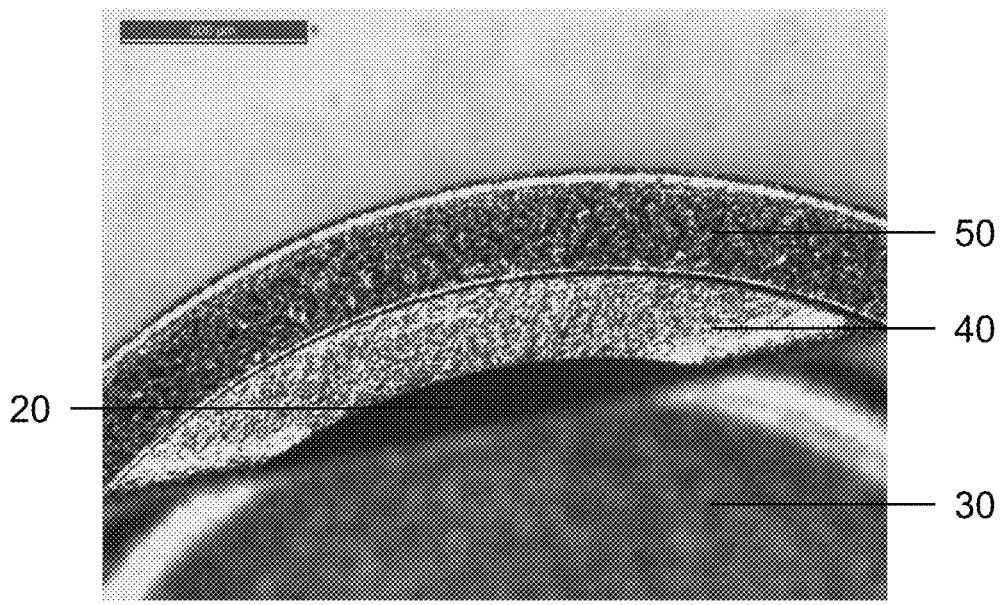

FIGS. 4(a) and 4(b) provide optical images of valve retainer 10 as exemplified in FIGS. 2(a) and 2(b), after 2 minutes of etch treatment as described above. The arrows mark horizontal WEDM plane 40.

Figure 5A:
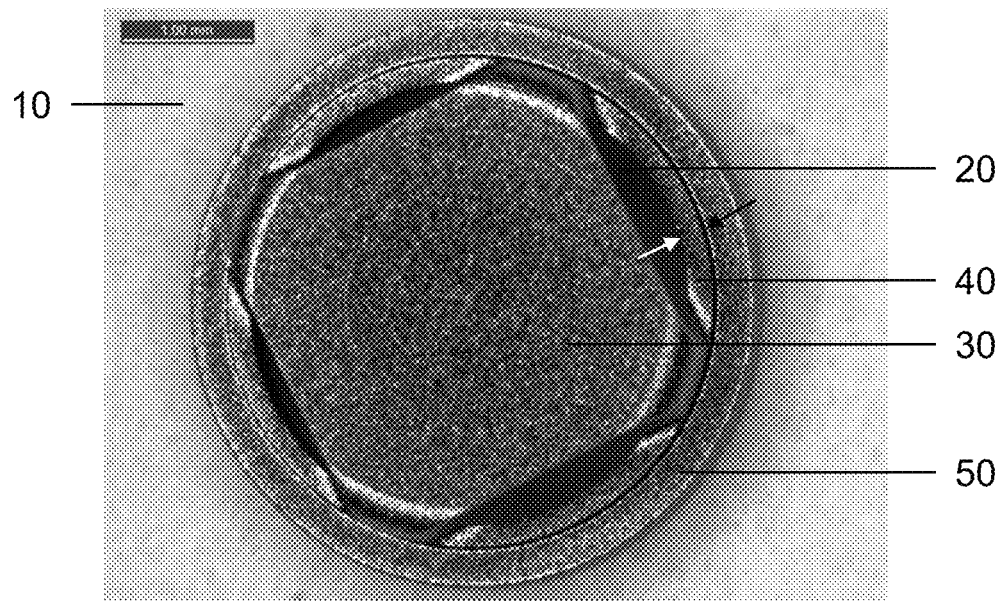
FIGS. 5(a) and 5(b) are optical images at two different magnifications of valve retainer 10 that was chemically etched for 3 minutes in 2 vol % HF in 30 vol % HNO$_3$ at room temperature with sonication (40 KHz), followed by rinsing and drying. The arrows mark the horizontal WEDM horizontal plane 40.
Figure 5B:
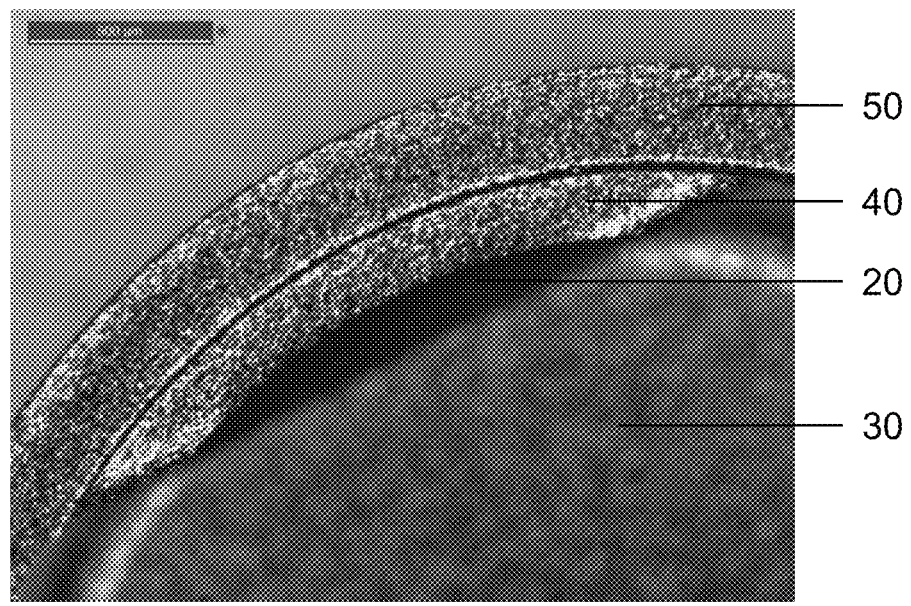

FIGS. 5(a) and 5(b) provide optical images of valve retainer 10 as exemplified in FIGS. 2(a) and 2(b), after 3 minutes of etch treatment as described above. The arrows mark horizontal WEDM plane 40.

Figure 6A:
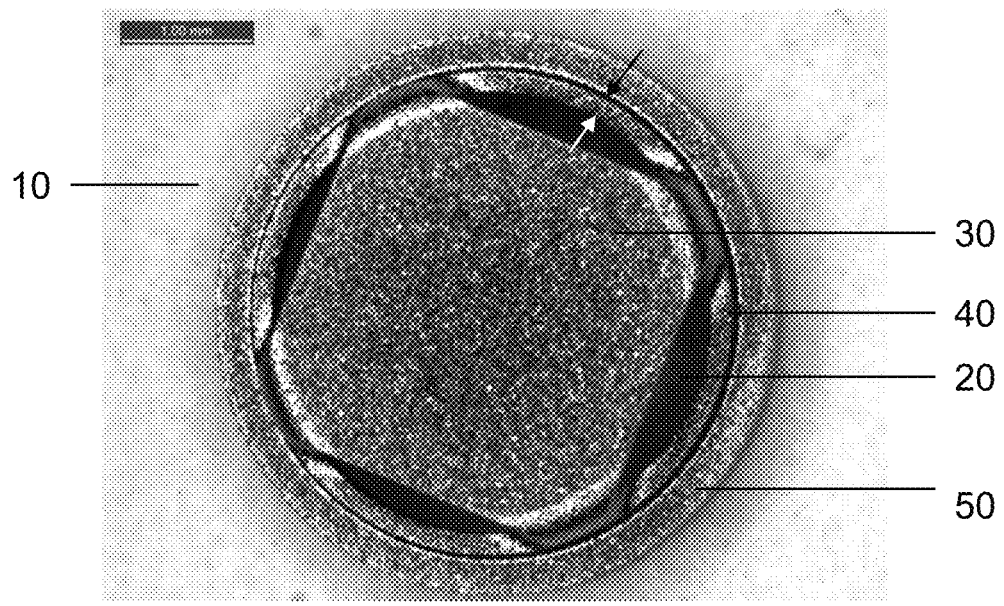
FIGS. 6(a) and 6(b) are optical images at two different magnifications of valve retainer 10 that was chemically etched for 4 minutes in 2 vol % HF in 30 vol % HNO$_3$ at room temperature with sonication (40 KHz), followed by rinsing and drying. The arrows mark the horizontal WEDM horizontal plane 40.
Figure 6B:
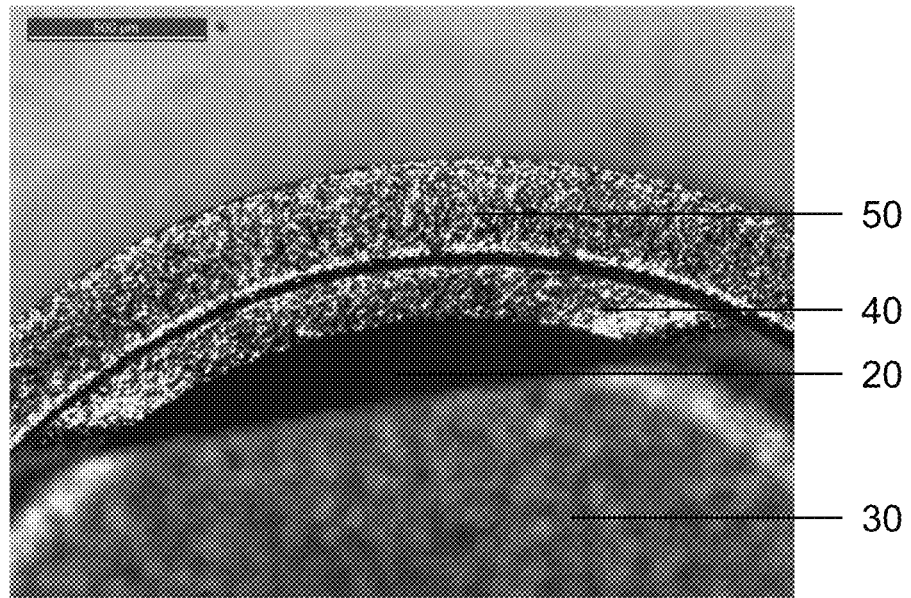

FIGS. 6(a) and 6(b) provide optical images of valve retainer 10 as exemplified in FIGS. 2(a) and 2(b), after 4 minutes of etch treatment as described above. The arrows mark horizontal WEDM plane 40.

Figure 7A:
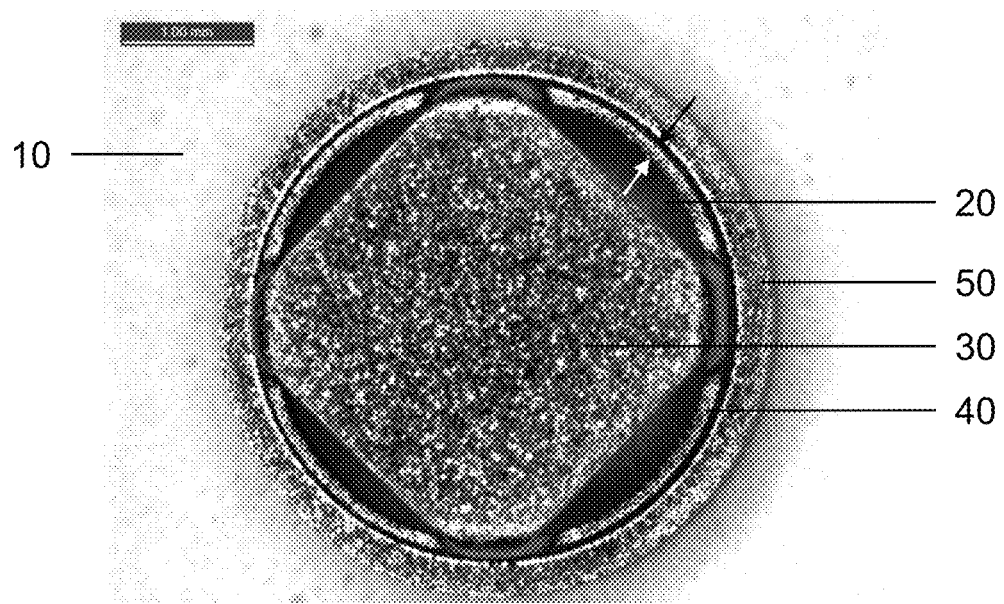
FIGS. 7(*a*) and 7(*b*) are optical images at two different magnifications of valve retainer 10 that was chemically etched for 5 minutes in 2 vol % HF in 30 vol % HNO$_3$ at room temperature with sonication (40 KHz), followed by rinsing and drying. The arrows mark the horizontal WEDM horizontal plane 40.
Figure 7B:
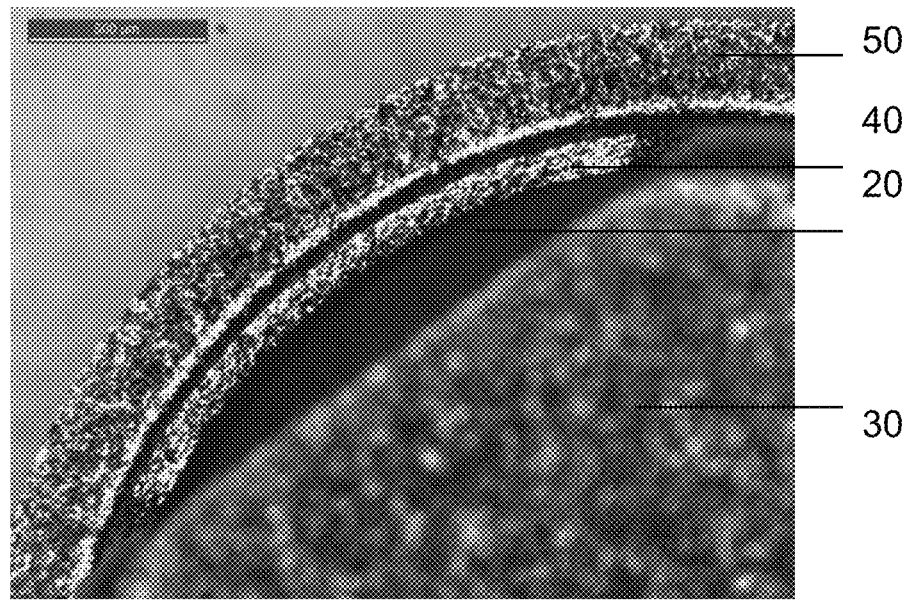

FIGS. 7(a) and 7(b) provide optical images of valve retainer 10 as exemplified in FIGS. 2(a) and 2(b), after 5 minutes of etch treatment as described above. The arrows mark horizontal WEDM plane 40.

It was found that with increased etching time, the vertical drug flow channels 20 increased in size with the removal of recast layer and/or splatter on the interior surfaces of the vertical drug flow channels 20.

Additionally, results based on the FIGS. 2(a) through 7(b), indicated that an etching process of about 2 minutes or less was sufficient to remove the recast layer and/or splatter.

Scanning Electron Microscopy (SEM)

FIGS. 8(a) through 8(h) provide representative top view SEM images from an as-received WEDM machined valve retainer 10 with vertical drug flow channels 20, top surface of valve retainer 30, horizontal WEDM plane 40 with a recast layer (roughened surface) and horizontal plane 50 (with recast splatter) of valve retainer 10.

Figure 8A:
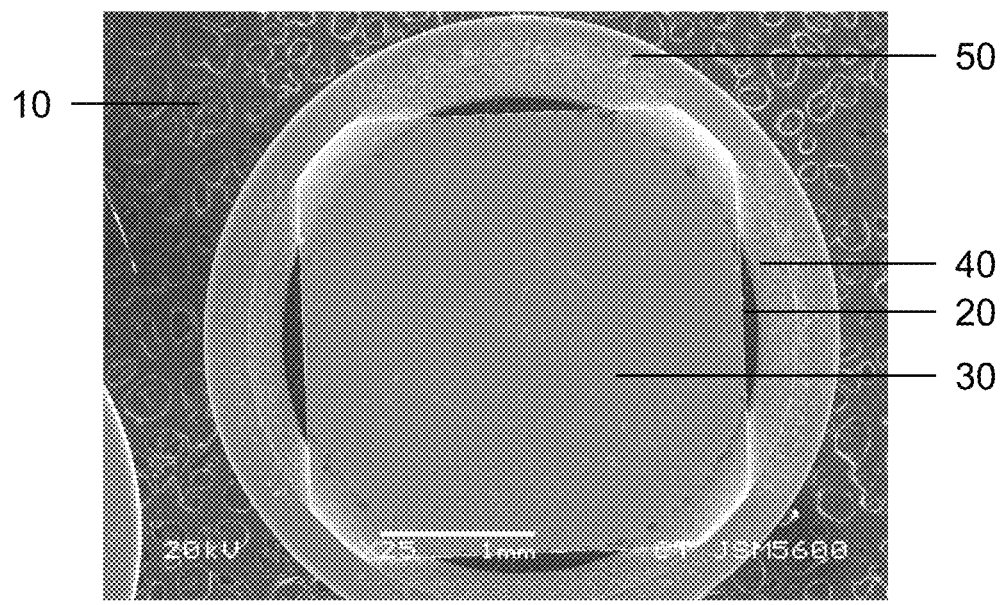
FIG. 8(*a*) is an SEM of an as-received WEDM treated valve retainer 10 from a top down perspective of valve retainer 10 with vertical drug flow channels 20, top surface of valve retainer 30, horizontal WEDM plane 40 with a recast layer (roughened surface) and horizontal plane 50 (with recast splatter).
Figure 8B:
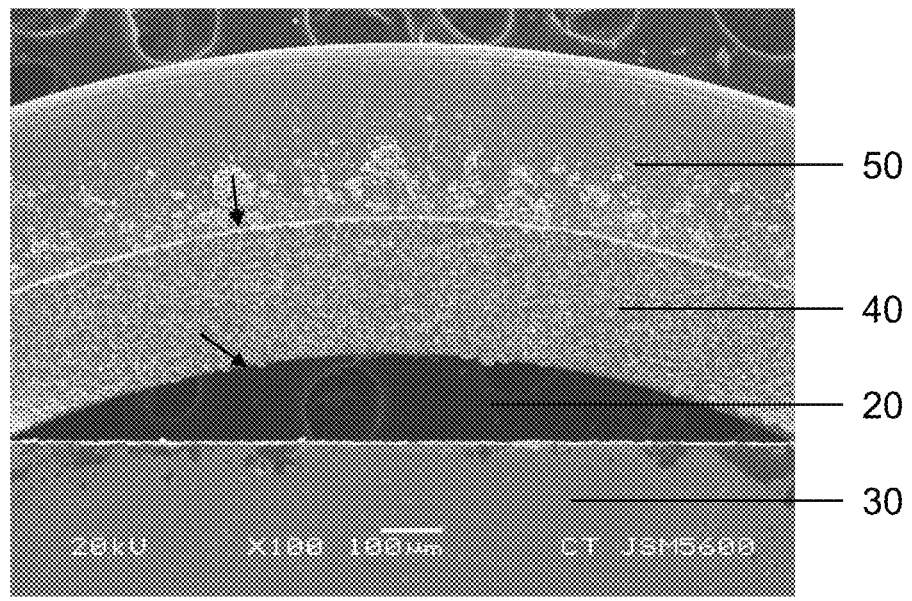

FIG. 8(b) provides a magnified SEM image of FIG. 8(a) showing top surface of valve retainer 30, vertical drug flow channel 20, horizontal WEDM plane with recast layer (roughened surface) and horizontal surface 50 with recast splatter. The arrows mark horizontal WEDM plane 40.

Figure 8C:
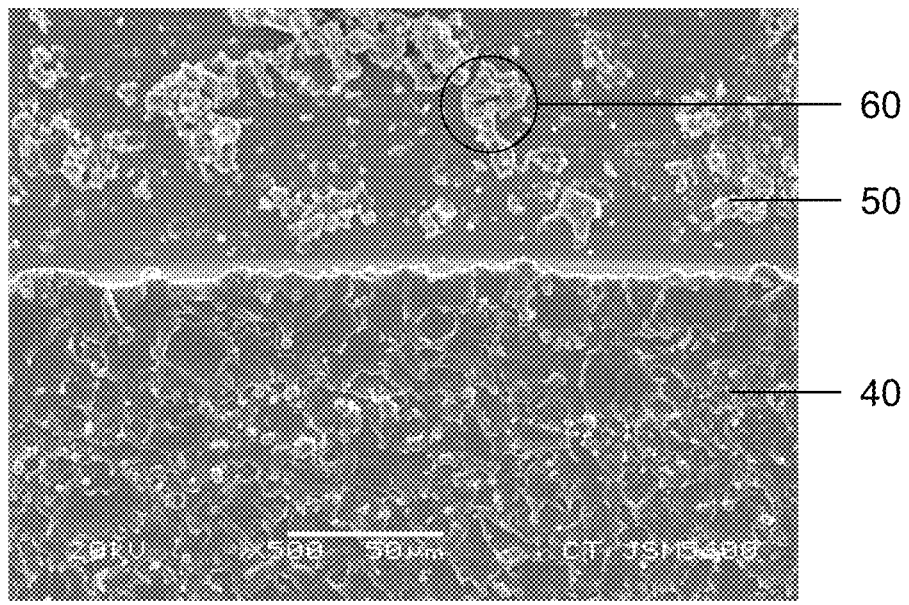

FIG. 8(c) is an SEM of increased magnification of FIG. 8(a) showing horizontal WEDM plane 40 with recast layer (flakey roughened surface) and horizontal surface 50 with recast splatter 60.

Figure 8D:
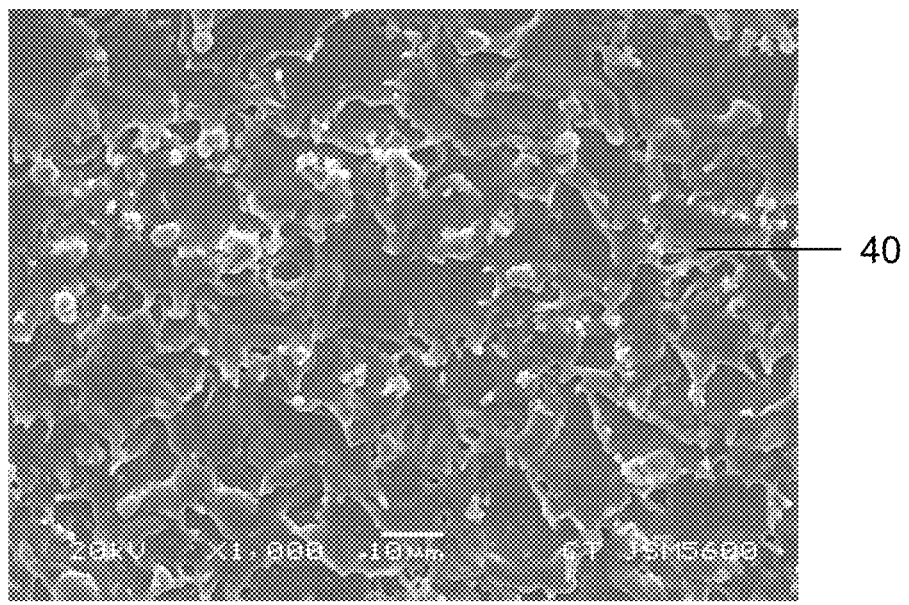

FIG. 8(d) is an SEM of FIG. 8(a) showing horizontal WEDM plane 40 with recast layer in the form of a roughened surface and/or flakes.

Figure 8E:
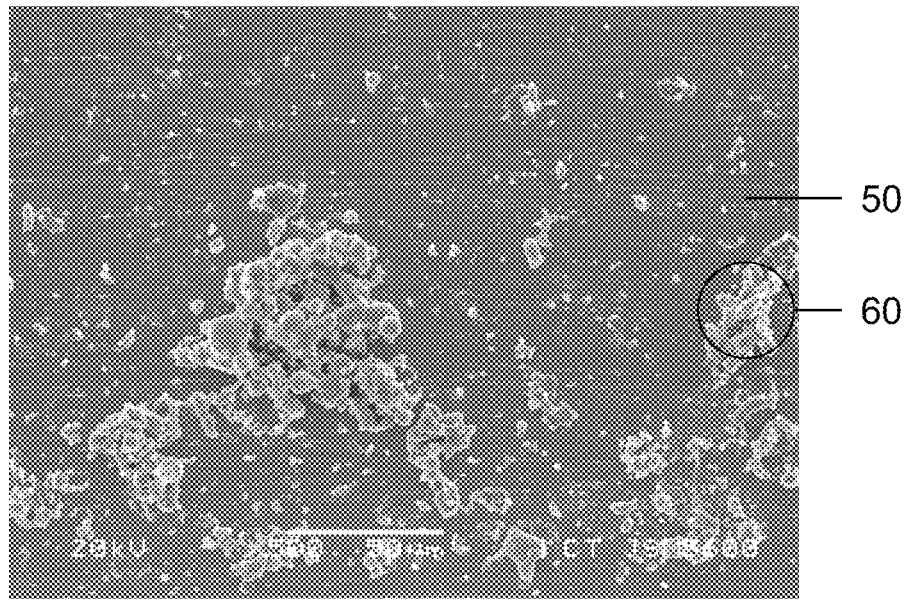
Figure 8F:
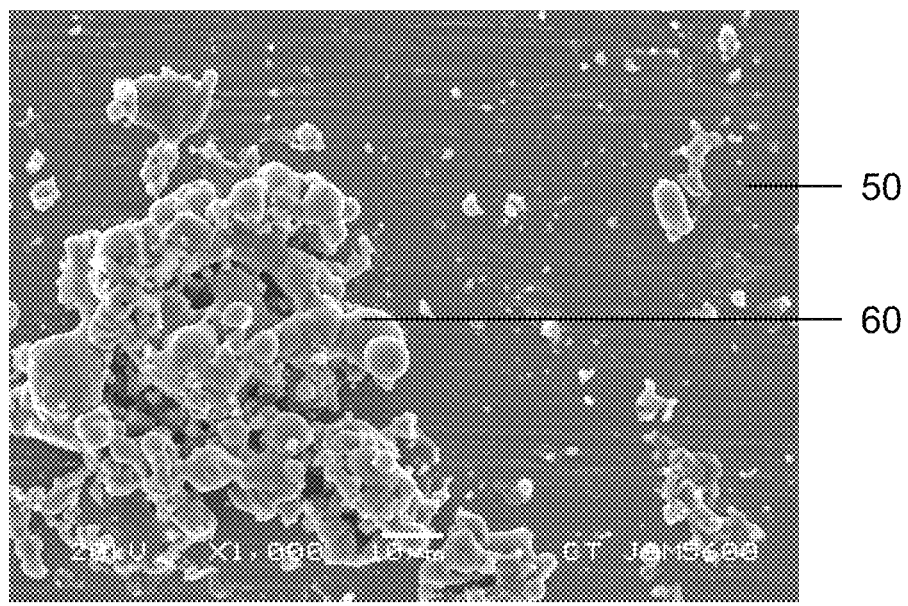

FIGS. 8(e) and 8(f) are SEMs at increased magnifications of the surface morphology of horizontal surface 50 of FIG. 8(a) with recast splatter 60. Horizontal surface 50 has a large amount of WEDM splatter 60 scattered on the surface. The WEDM splatter 60 varies in size from submicron to over 100 microns. The splatter 60 should be removed because it could adversely affect the function of the device.

Figure 8G:
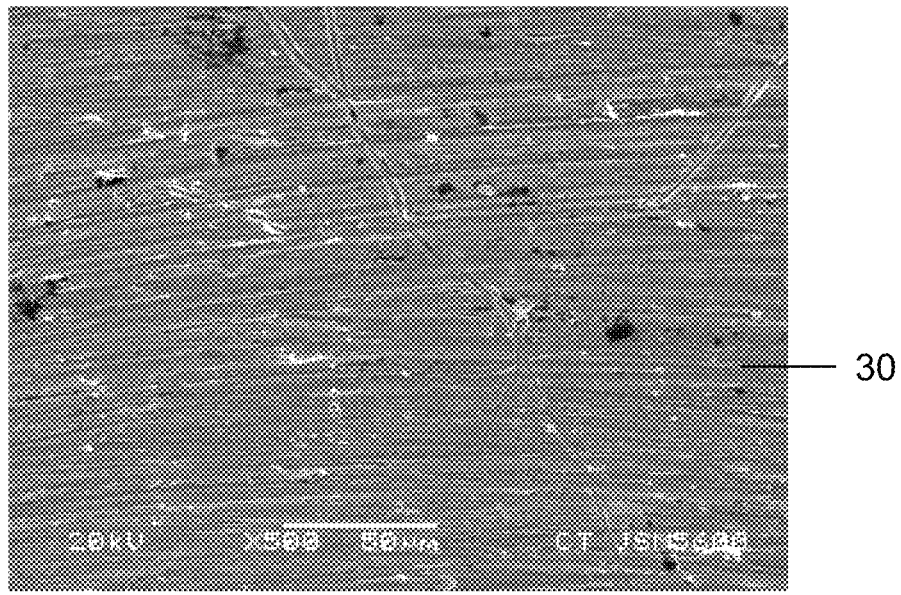
Figure 8H:
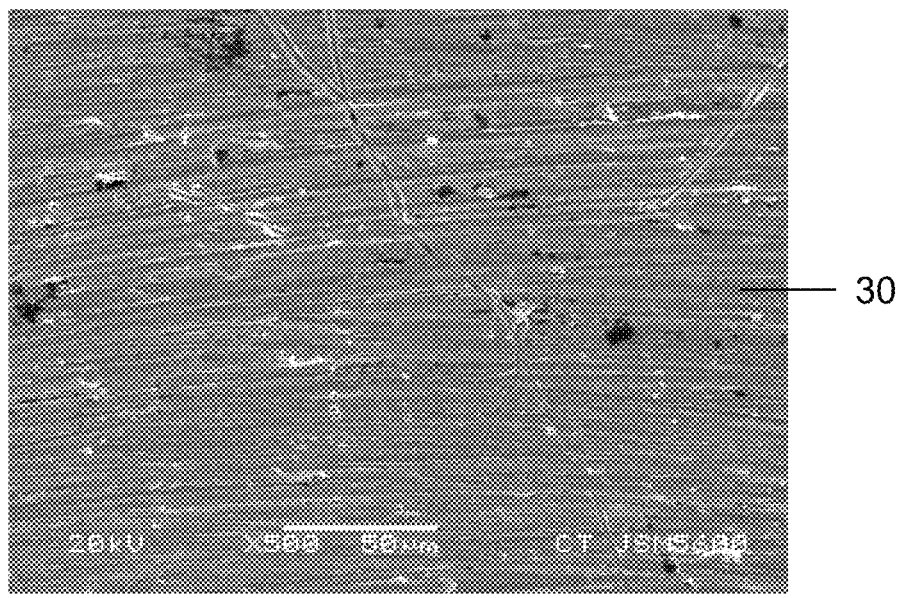

FIGS. 8(g) and 8(h) are SEMS at increased magnifications of the surface morphology of top surface of valve retainer 30 of FIG. 8(a). The top surface of valve retainer 30 shows a typical machined finish, free of splatters except at the WEDM cut edge.

Figure 9A:
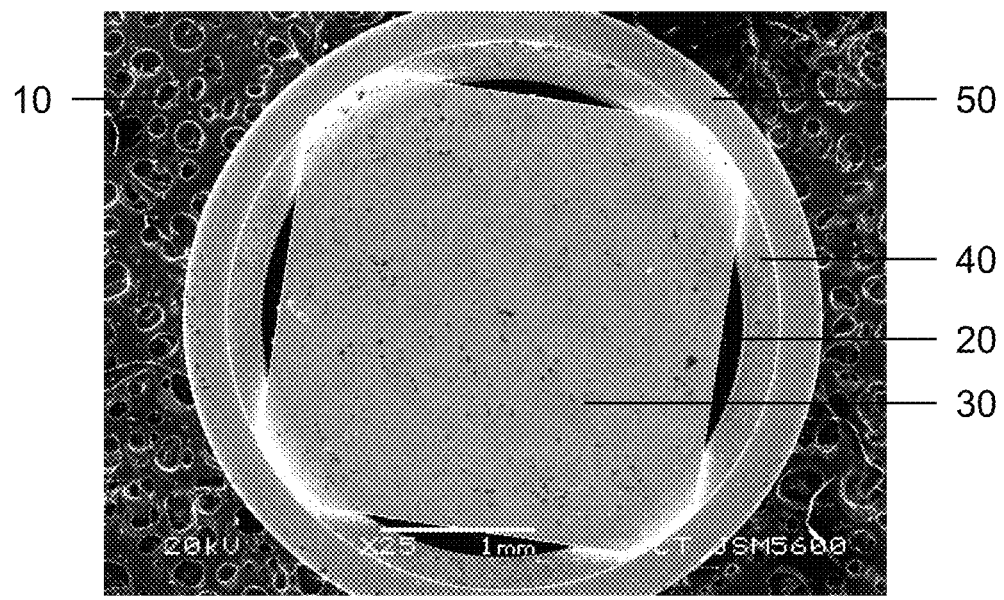
FIG. 9(*a*) provides an SEM of valve retainer 10 as exemplified in FIG. 8(*a*) after 1 minute of etching with 2 vol % HF in 30 vol % HNO$_3$ acid at room temperature with sonication (40 KHz), followed by rinsing and drying.

FIG. 9(a) provides a top view SEM of valve retainer 10 as exemplified in FIG. 8(a) after 1 minute of etch treatment as described above.

Figure 9B:
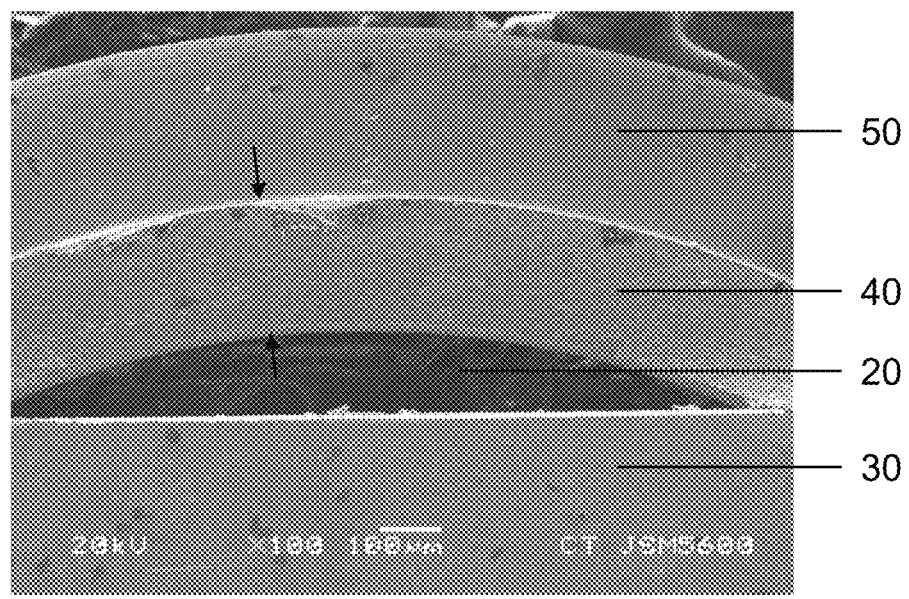

FIGS. 9(b), (c), and (d) are successive higher magnification SEM images of FIG. 9(a) after 1 minute of etch treatment as described above.

FIG. 9(b) provides a magnified SEM image of FIG. 9(a) showing top surface of valve retainer 30, vertical drug flow channel 20, horizontal WEDM plane with recast layer (roughened surface) removed and horizontal surface 50 with recast splatter removed after 1 minute of etch treatment as described above. The arrows mark horizontal WEDM plane 40.

Figure 9C:
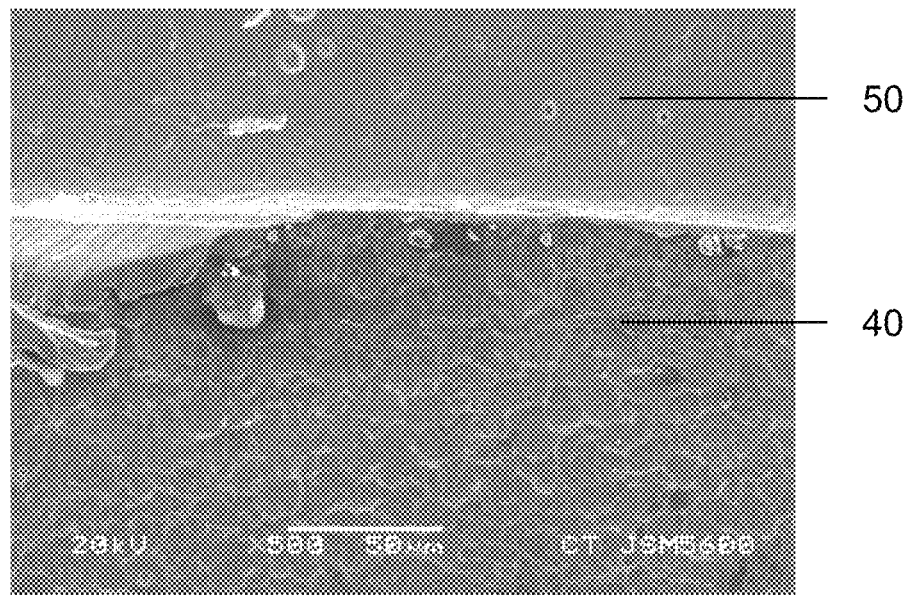

FIG. 9(c) is an SEM of increased magnification of FIG. 9(a) showing horizontal WEDM plane 40 with recast layer (flakey roughened surface) removed and horizontal surface 50 with recast splatter 60 removed after 1 minute of etch treatment as described above.

Figure 9D:
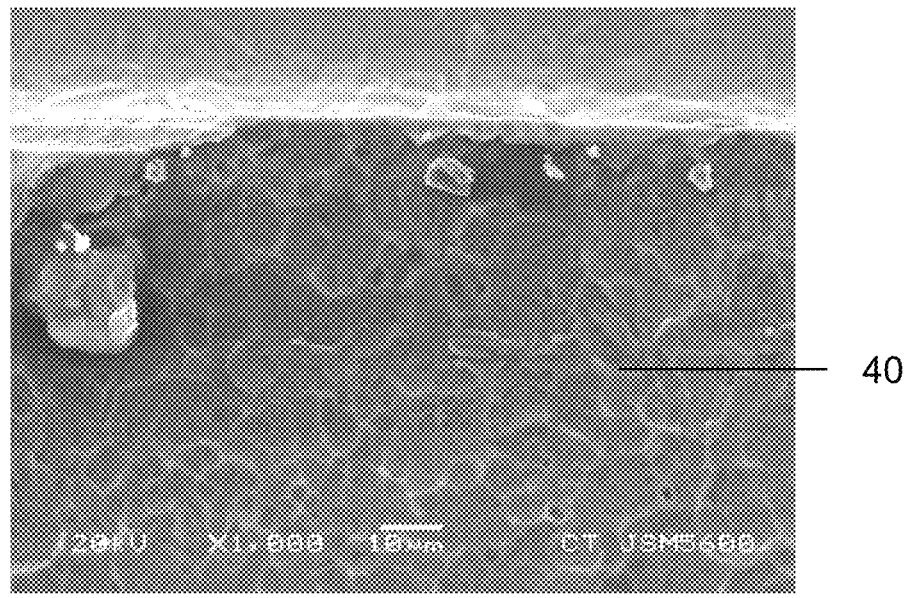

FIG. 9(d) is an SEM of FIG. 9(a) showing horizontal WEDM plane 40 without the recast layer after 1 minute of etch treatment as described above.

Figure 9E:
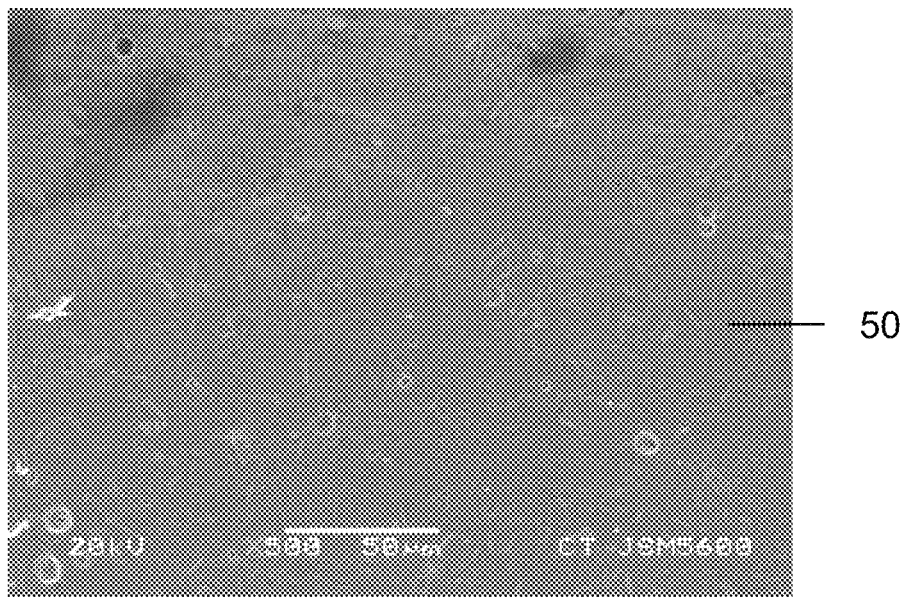
Figure 9F:
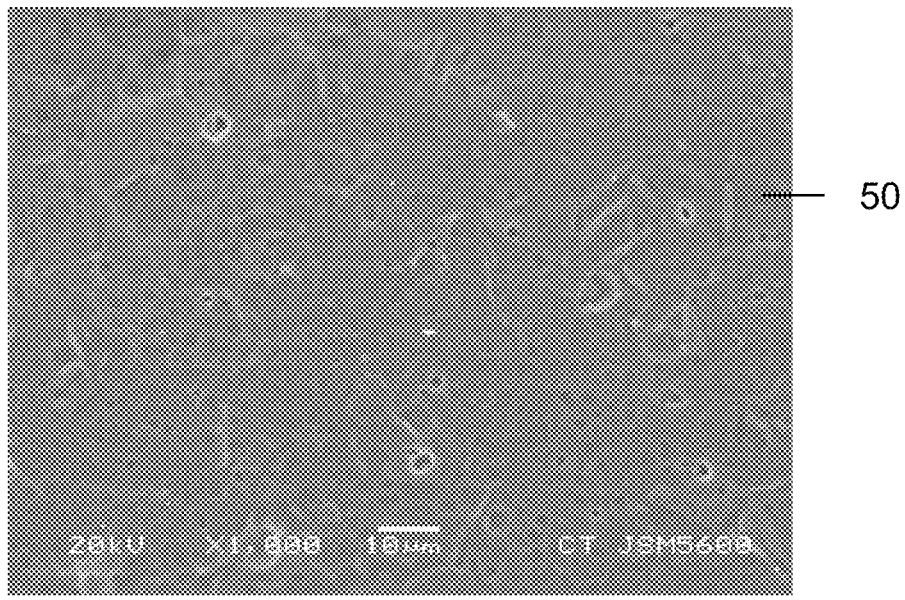

FIGS. 9(e) and 9(f) are SEMs at increased magnifications of the surface morphology of horizontal surface 50 of FIG. 9(a) without recast splatter 60 after 1 minute of etch treatment as described above. Minor etching can be seen on the horizontal surface 50 and the top surface of valve retainer 30. As shown in FIGS. 9 (e) and (f), horizontal surface 50 is splatter free after of 1 minute of etching.

Figure 9G:
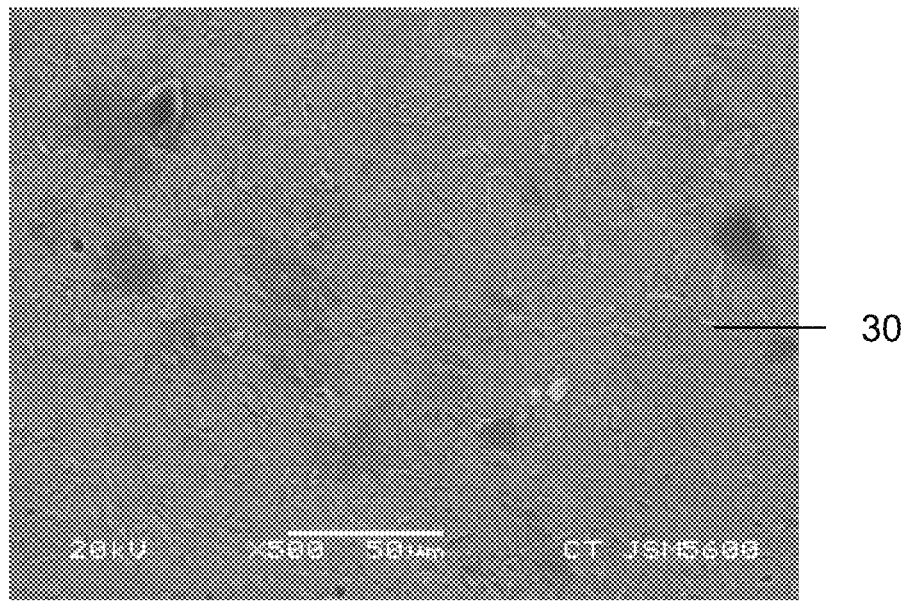
Figure 9H:
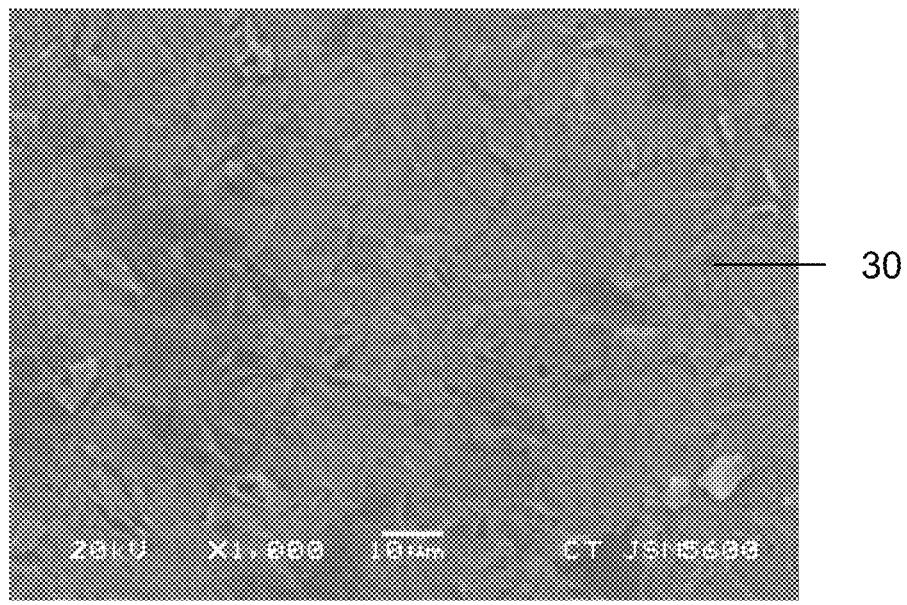

FIGS. 9(g) and 9(h) are SEMS at increased magnifications of the surface morphology of top surface of valve retainer 30 of FIG. 9(a) after 1 minute of etch treatment as described above.

Figure 10A:
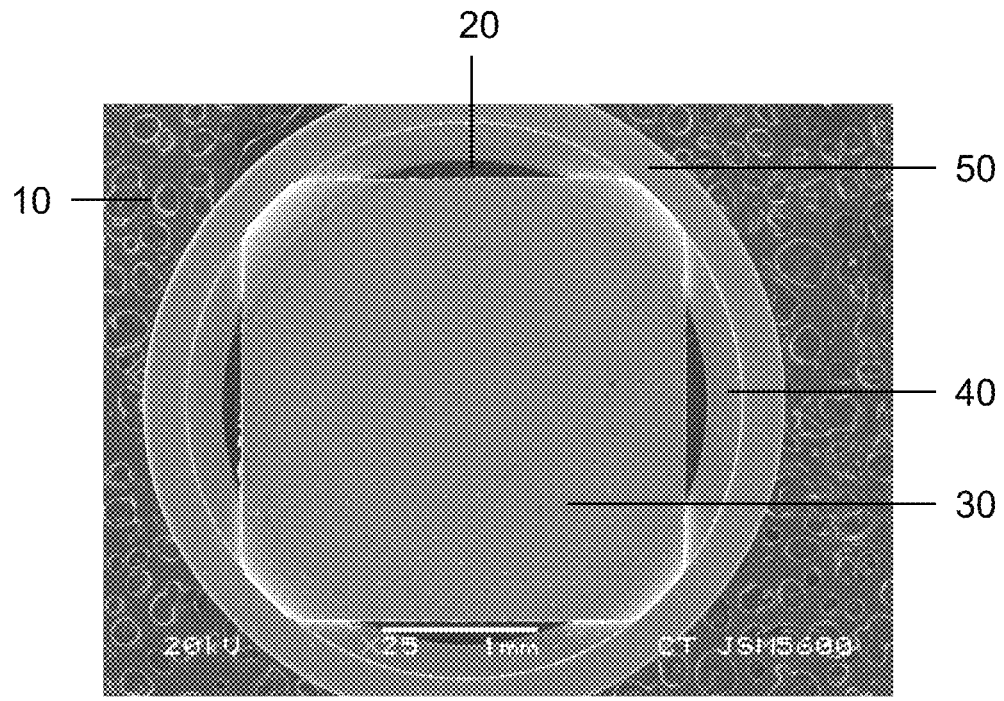
FIG. 10(*a*) provides an SEM of valve retainer 10 as exemplified in FIG. 8(*a*) after 2 minutes of etching with 2 vol % HF in 30 vol % HNO$_3$ acid at room temperature with sonication (40 KHz), followed by rinsing and drying.

FIG. 10(a) provides a top view SEM of valve retainer 10 as exemplified in FIG. 8(a) after 2 minutes of etching etch treatment as described above.

Figure 10B:
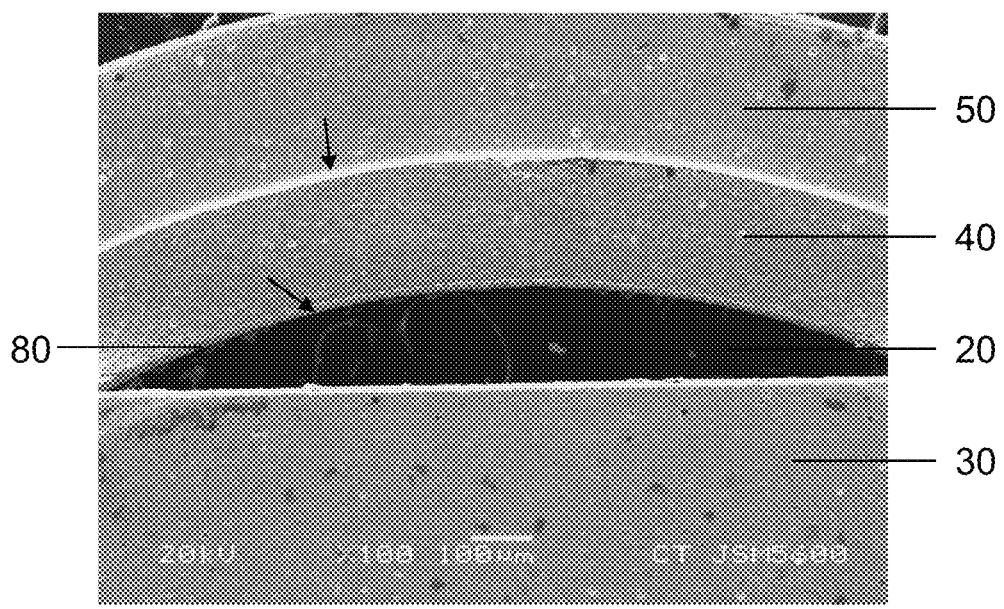

FIGS. 10(b), (c), and (d) are successive higher magnification SEM images of FIG. 10(a) after 2 minutes of etch treatment as described above.

FIG. 10(b) provides a magnified SEM image of FIG. 10(a) showing top surface of valve retainer 30, vertical drug flow channel 20, horizontal WEDM plane 40 without recast layer (roughened surface) and horizontal surface 50 without recast splatter after 2 minutes of etch treatment as described above. The arrows mark horizontal WEDM plane 40.

Figure 10C:
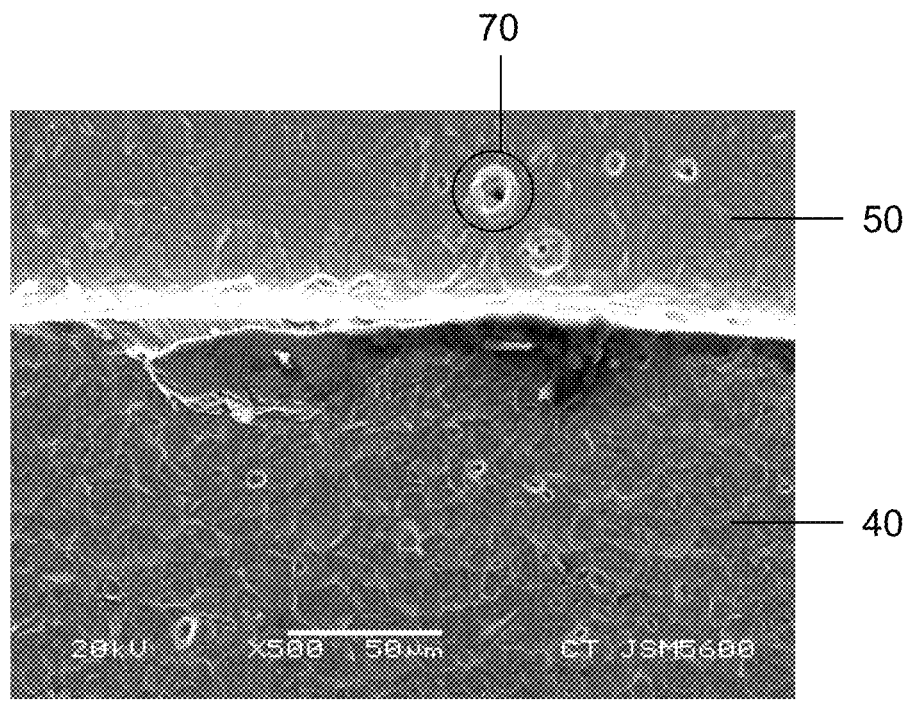

FIG. 10(c) is an SEM of increased magnification of FIG. 10(a) showing horizontal WEDM plane 40 without recast layer and horizontal surface 50 without recast splatter 60 after 2 minutes etch treatment as described above. Etch pits 70 in the titanium surface were now noted.

Figure 10D:
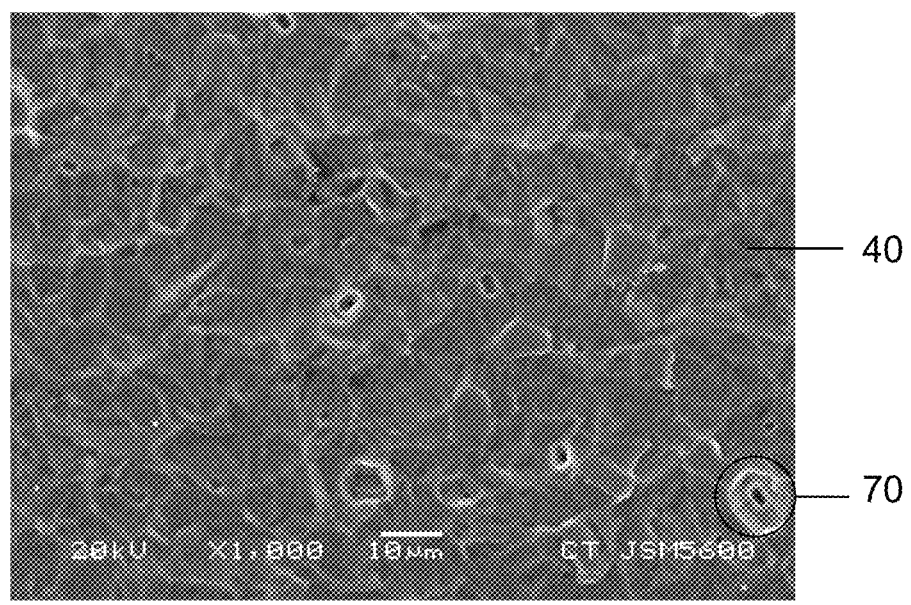

FIG. 10(d) is an SEM of FIG. 10(a) showing horizontal WEDM plane 40 with etch pits 70 after 2 minutes of etch treatment as described above.

Figure 10E:
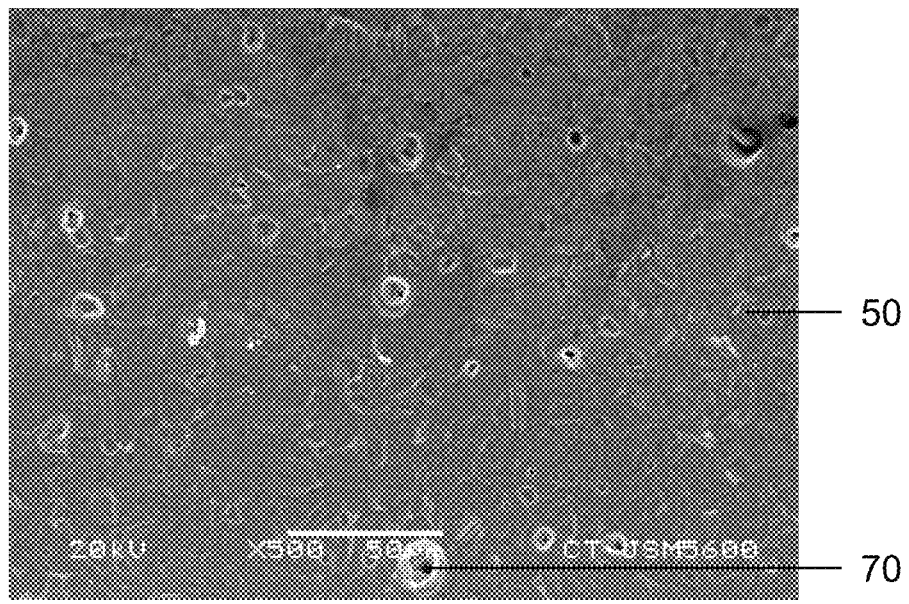
Figure 10F:
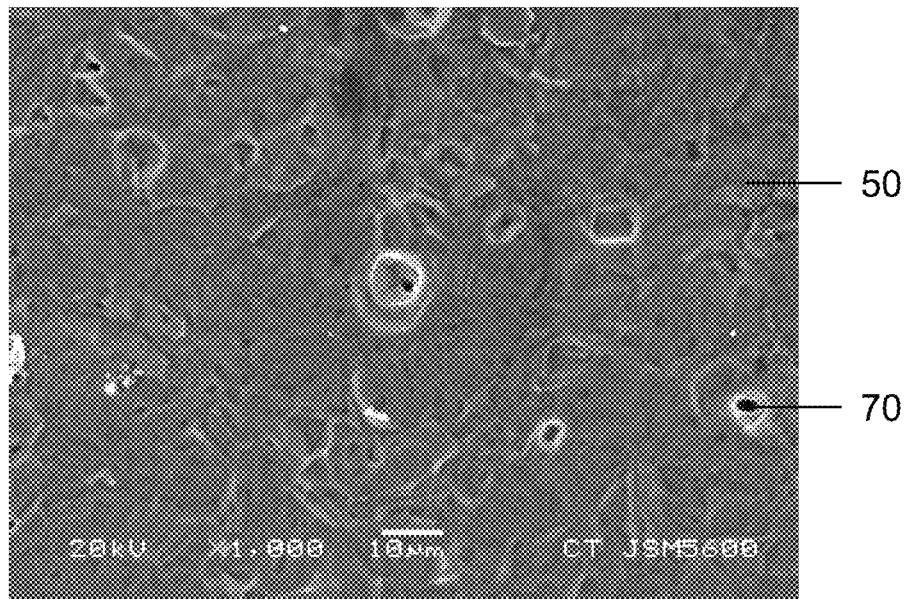

FIGS. 10(e) and 10(f) are SEMs at increased magnifications of the surface morphology of horizontal surface 50 of FIG. 10(a) with etch pits 70 after 2 minutes of etch treatment as described above. Small etch pits can be seen on the horizontal WEDM plane 40 as well as on the horizontal surface 50 and the top surface of the valve retainer 30. FIGS. 10(e) and 10(f) show that the horizontal surface 50 is splatter free after 2 minutes of etching.

Figure 10G:
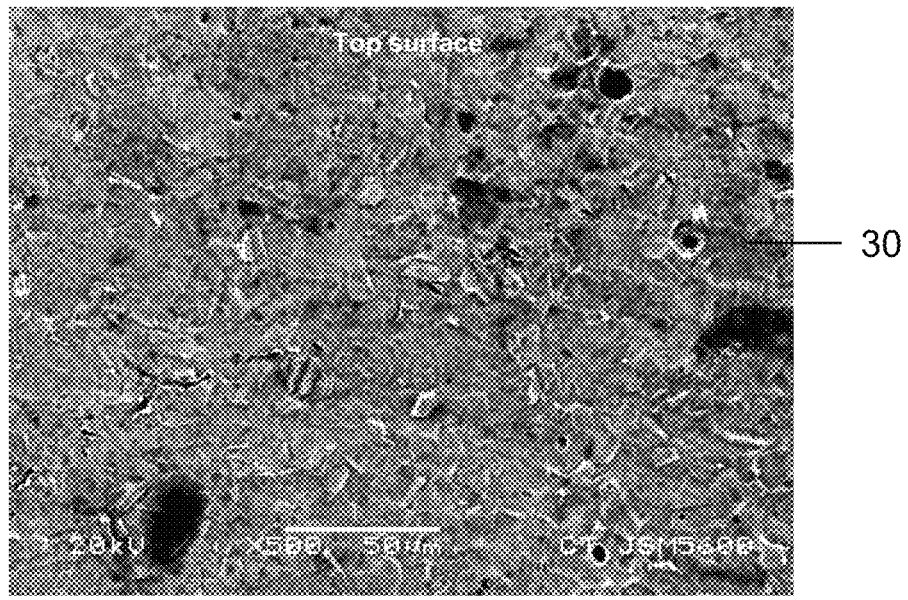
Figure 10H:
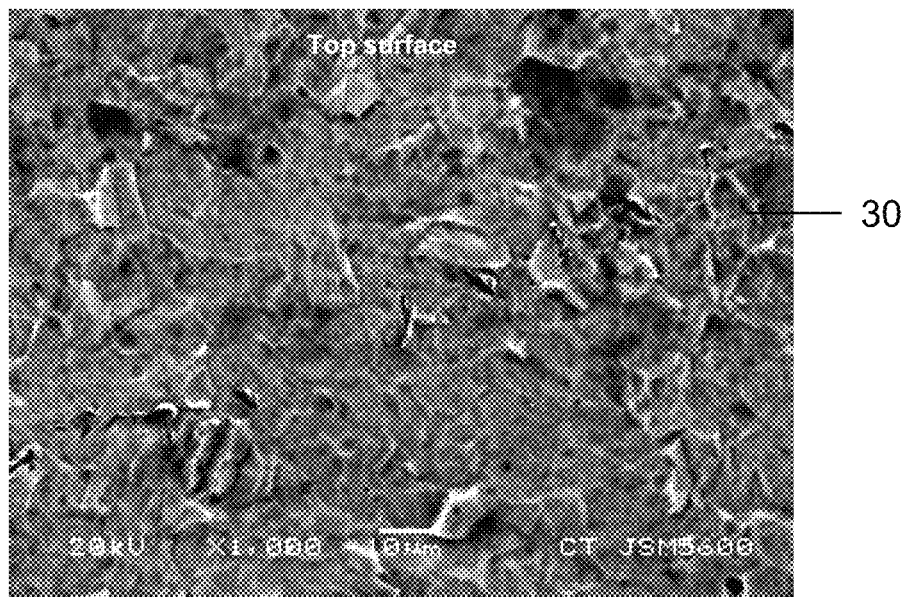

FIGS. 10(g) and 10(h) are SEMS at increased magnifications of the surface morphology of top surface of valve retainer 30 of FIG. 10(a) after 2 minutes of etch treatment as described above.

Figure 11A:
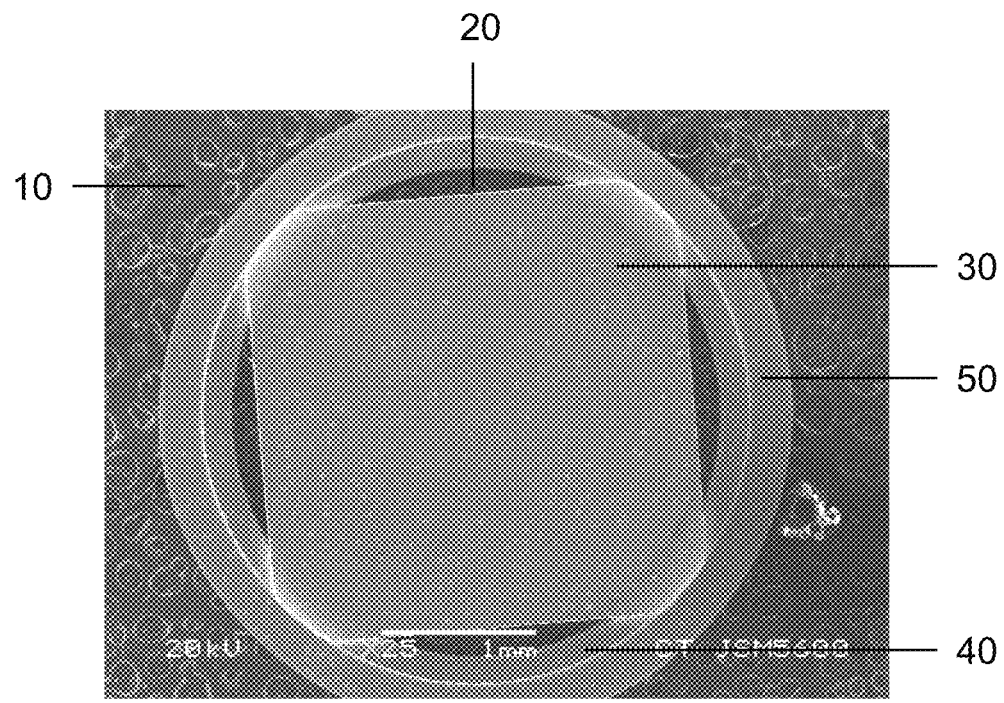
FIG. 11(*a*) provides an SEM of valve retainer 10 as exemplified in FIG. 8(*a*) after 3 minutes of etching with 2 vol % HF in 30 vol % HNO$_3$ acid at room temperature with sonication (40 KHz), followed by rinsing and drying.
FIG. 11(d) is an SEM of FIG. 11(a) showing horizontal WEDM plane 40 with etch pits 70 after 3 minutes of etching with 2 vol % HF in 30 vol % HNO$_3$ acid at room temperature with sonication (40 KHz), followed by rinsing and drying.
FIGS. 11(e) and 11(f) are SEMs at increased magnifications of the surface morphology of horizontal surface 50 with etch pits 70 after 3 minutes of etching with 2 vol % HF in 30 vol % HNO$_3$ acid at room temperature with sonication (40 KHz), followed by rinsing and drying.
FIGS. 11(g) and 11(h) are SEMS at increased magnifications of the surface morphology of top surface of valve retainer 30 after 3 minutes of etching with 2 vol % HF in 30 vol % HNO$_3$ acid at room temperature with sonication (40 KHz), followed by rinsing and drying. Etch pits 70 are noted.

FIG. 11(a) provides an SEM of valve retainer 10 as exemplified in FIG. 8(a) after 3 minutes of etch treatment as described above.

Figure 11B:
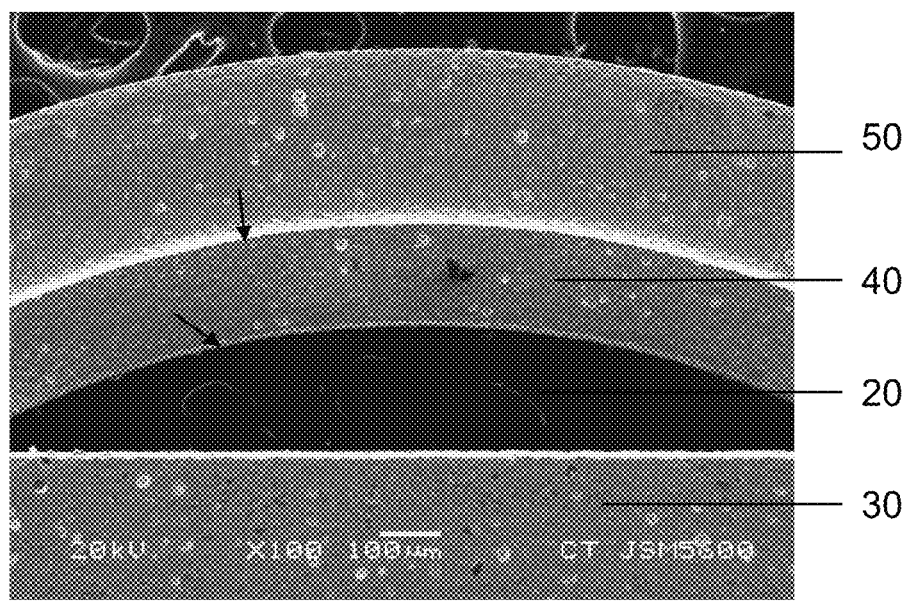

FIGS. 11(b), (c), and (d) are successive higher magnification SEM images of FIG. 11(a) after 3 minutes of etch treatment as described above.

FIG. 11(b) provides a magnified SEM image of FIG. 11(a) showing top surface of valve retainer 30, vertical drug flow channel 20, horizontal WEDM plane 40 without recast layer (roughened surface) and horizontal surface 50 without recast splatter 60 after 3 minutes of etch treatment as described above. Etch pits 70 were noted on the titanium surface. The arrows mark horizontal WEDM plane 40.

Figure 11C:
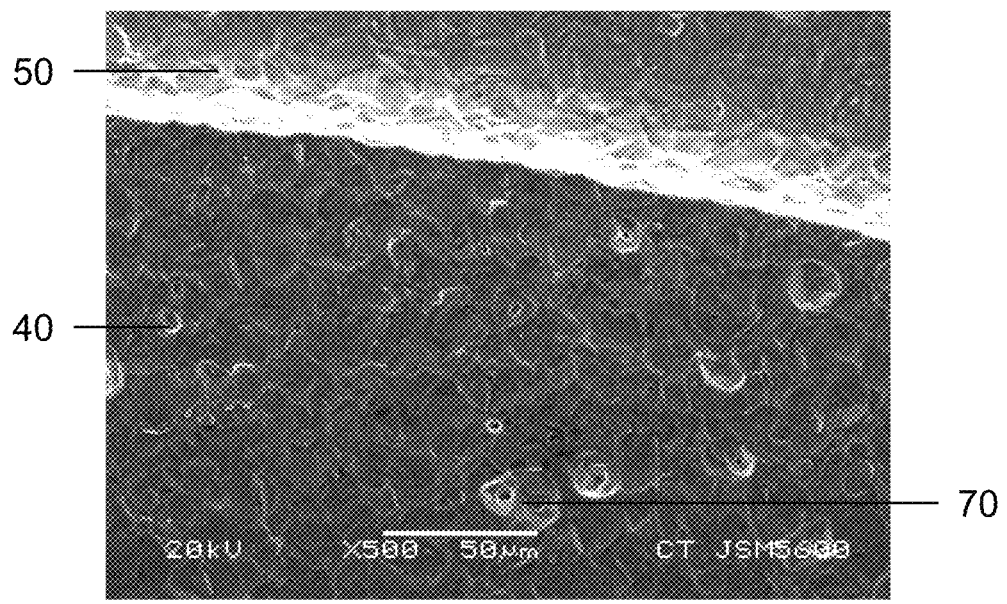

FIG. 11(c) is an SEM of increased magnification of FIG. 11(a) showing horizontal WEDM plane 40 without recast layer and horizontal surface 50 without recast splatter 60 after 3 minutes of etch treatment as described above. Etch pits 70 in the titanium surface were noted.

Figure 11D:
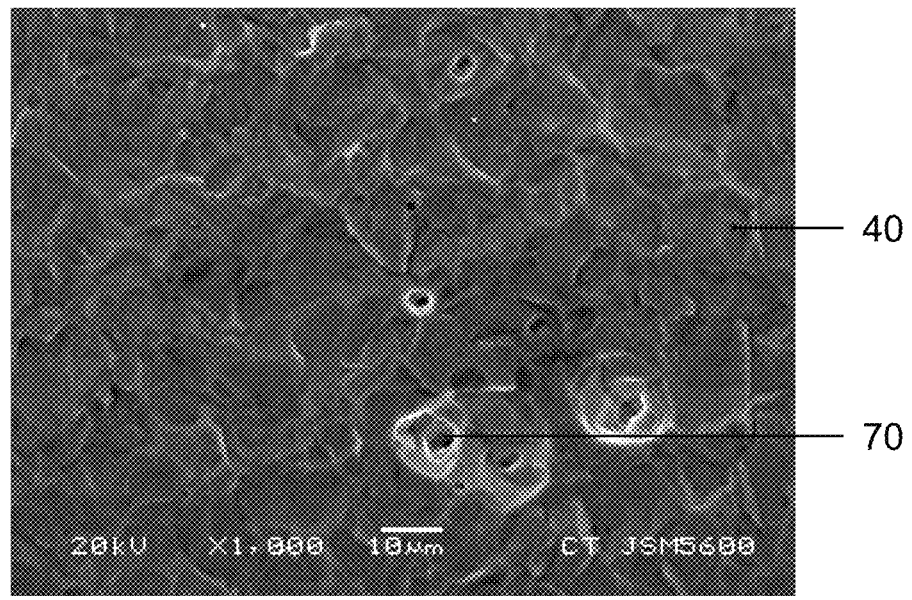

FIG. 11(d) is an SEM of FIG. 11(a) showing horizontal WEDM plane 40 with etch pits 70 after 3 minutes of etch treatment as described above.

Figure 11E:
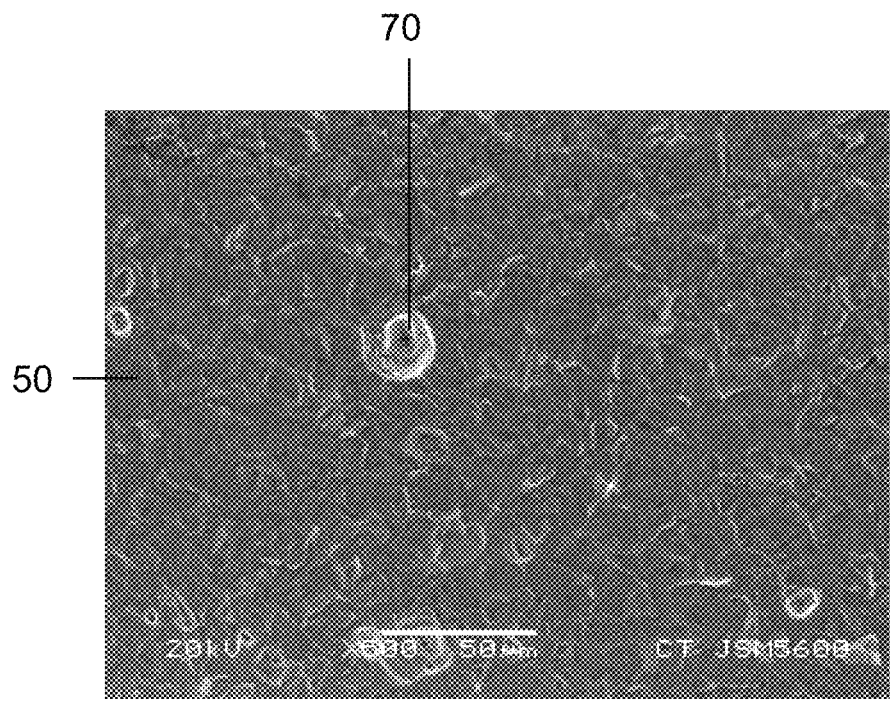
Figure 11F:
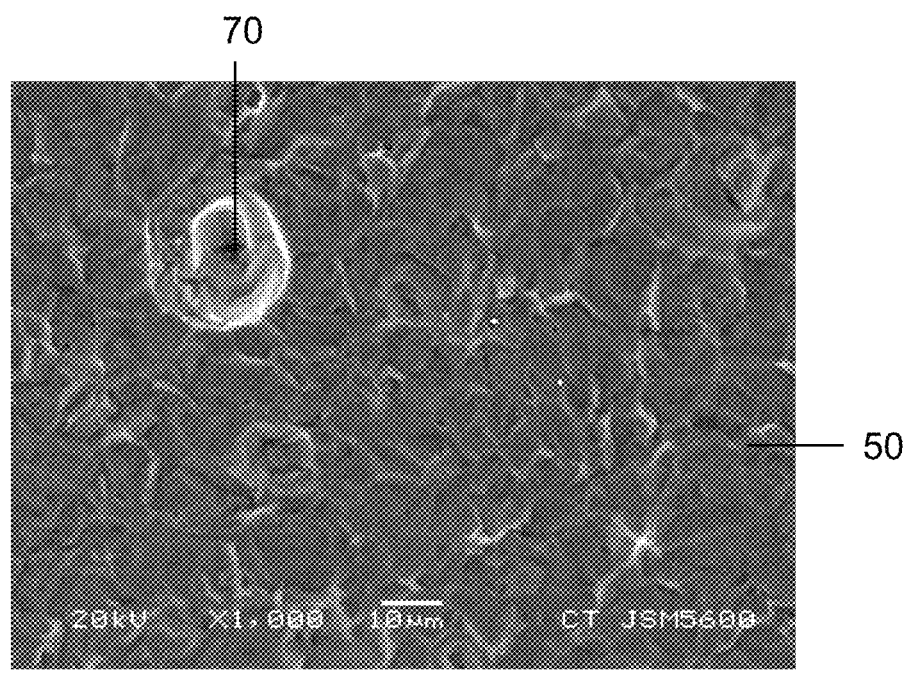

FIGS. 11(e) and 11(f) are SEMs at increased magnifications of the surface morphology of horizontal surface 50 of FIG. 11(a) with etch pits 70 after 3 minutes of etch treatment as described above.

Figure 11G:
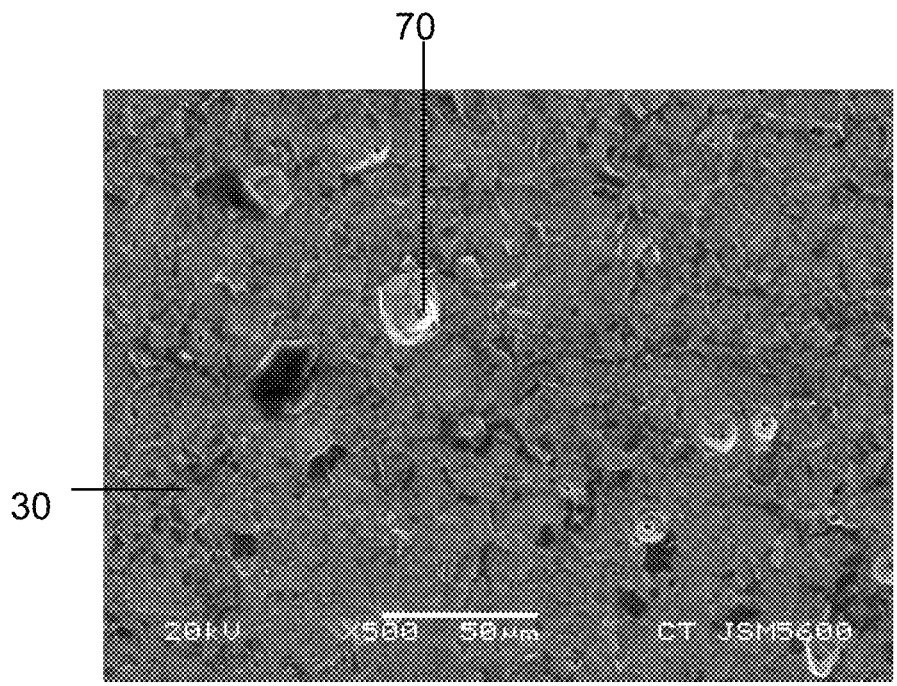
Figure 11H:
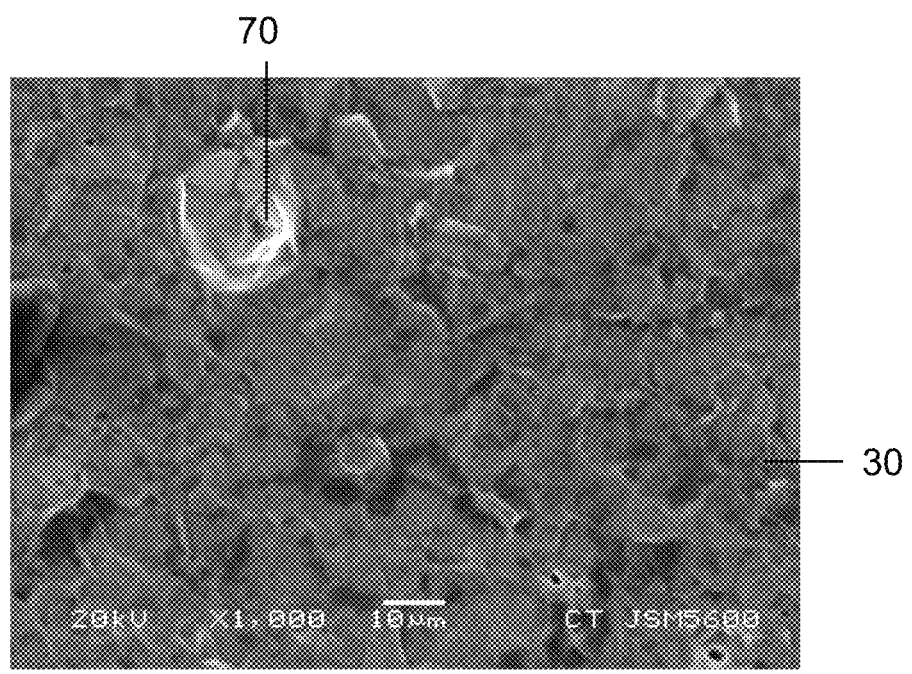

FIGS. 11(g) and 11(h) are SEMS at increased magnifications of the surface morphology of top surface of valve retainer 30 of FIG. 11(a) after 3 minutes of etch treatment as described above.

FIGS. 11(c) and 11(d) show typical etched morphology on the Ti substrate after the WEDM recast layer was removed. Small etch pits 70 can be seen on the horizontal WEDM plane 40 as well as the horizontal surface 50 and the top surface of valve retainer 30.

Figure 12A:
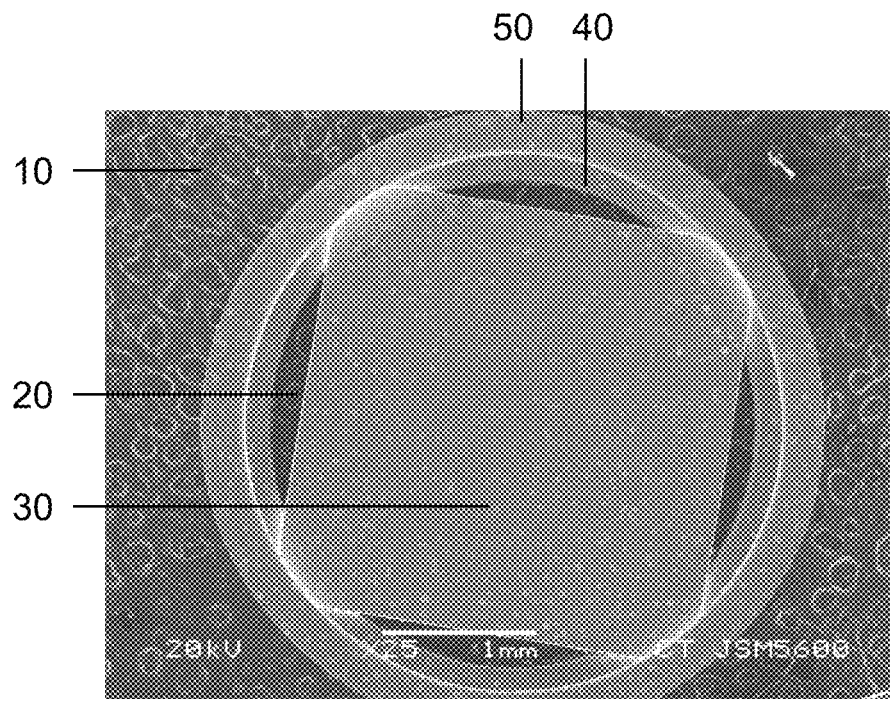
FIG. 12(a) provides an SEM of valve retainer 10 as exemplified in FIG. 8(a) after 4 minutes of etching with 2 vol % HF in 30 vol % HNO$_3$ acid at room temperature with sonication (40 KHz), followed by rinsing and drying.

FIG. 12(a) provides an SEM of valve retainer 10 as exemplified in FIG. 8(a) after 4 minutes of etch treatment as described above.

Figure 12B:
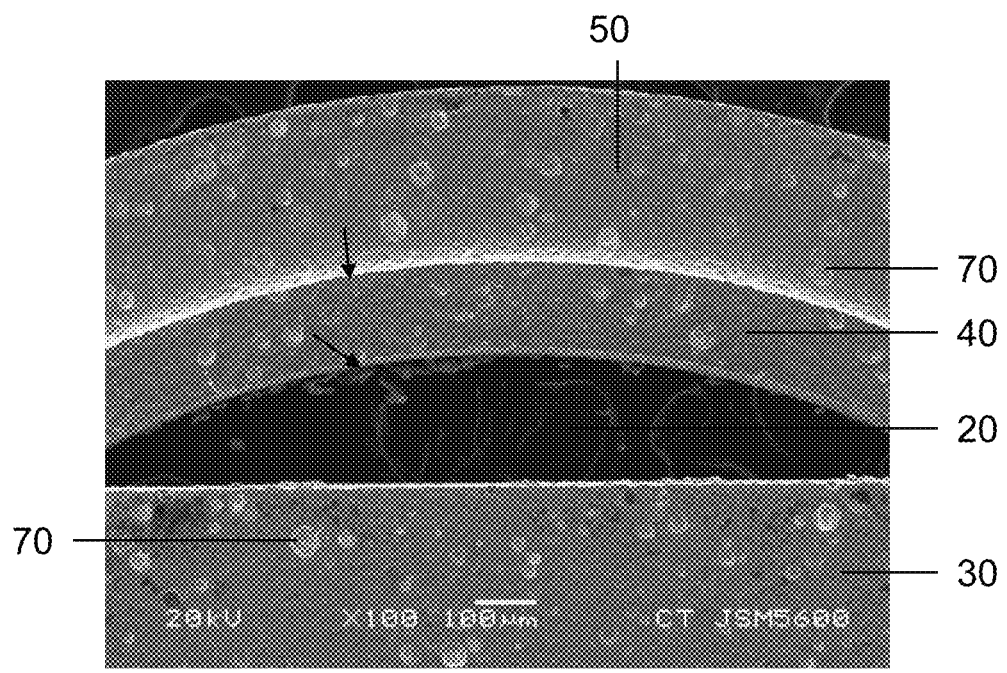
FIGS. 12(b), (c), and (d) are successive higher magnification SEM images of FIG. 12(a) after 4 minutes of etching with 2 vol % HF in 30 vol % HNO$_3$ acid at room temperature with sonication (40 KHz), followed by rinsing and drying.

FIGS. 12(b), (c), and (d) are successive higher magnification SEM images of FIG. 12(a) after 4 minutes of etch treatment as described above.

FIG. 12(b) provides a magnified SEM image of FIG. 12(a) showing top surface of valve retainer 30, vertical drug flow channel 20, horizontal WEDM plane without recast layer (roughened surface) and horizontal surface 50 without recast splatter 60 after 4 minutes of etch treatment as described above. Etch pits 70 were noted on the titanium surface. The arrows mark horizontal WEDM plane 40.

Figure 12C:
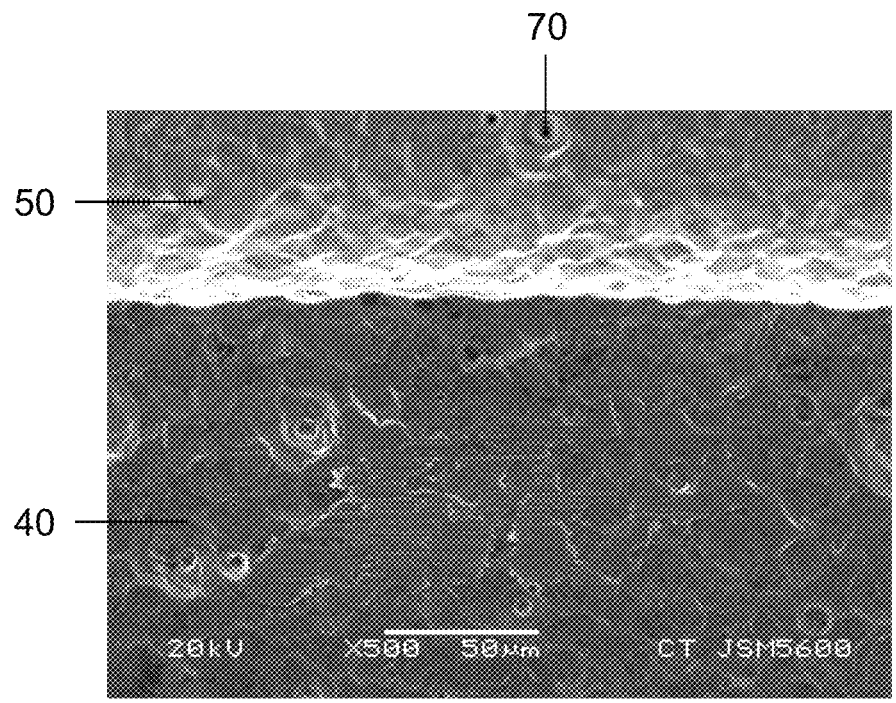
FIG. 12(c) is an SEM of increased magnification of FIG. 12(a) showing horizontal WEDM plane 40 without recast layer and horizontal surface 50 without recast splatter 60 after 4 minutes of etching with 2 vol % HF in 30 vol % HNO$_3$ acid at room temperature with sonication (40 KHz), followed by rinsing and drying. Etch pits 70 in the titanium surface were noted.

FIG. 12(c) is an SEM of increased magnification of FIG. 12(a) showing horizontal WEDM plane 40 without recast layer and horizontal surface 50 without recast splatter 60 after 4 minutes of etch treatment as described above. Etch pits 70 in the titanium surface were noted.

Figure 12D:
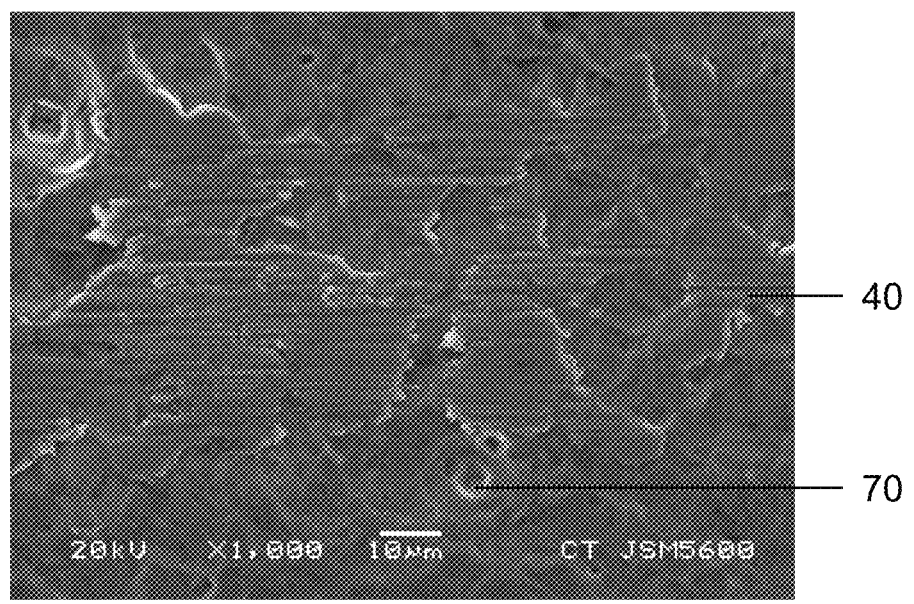
FIG. 12(d) is an SEM of FIG. 12(a) showing horizontal WEDM plane 40 with etch pits 70 after 4 minutes of etching with 2 vol % HF in 30 vol % HNO$_3$ acid at room temperature with sonication (40 KHz), followed by rinsing and drying.

FIG. 12(d) is an SEM of FIG. 12(a) showing horizontal WEDM plane 40 with etch pits 70 after 4 minutes of etch treatment as described above.

Figure 12E:
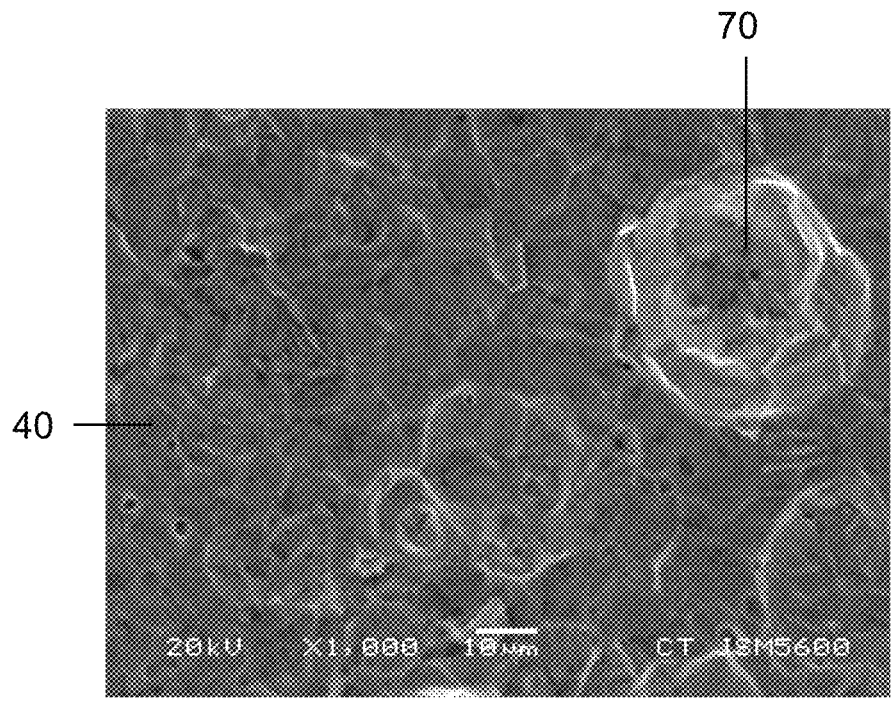
FIGS. 12(e) and 12(f) are SEMs at increased magnifications of the surface morphology of horizontal surface 50 with etch pits 70 after 4 minutes of etching with 2 vol % HF in 30 vol % HNO$_3$ acid at room temperature with sonication (40 KHz), followed by rinsing and drying.
Figure 12F:
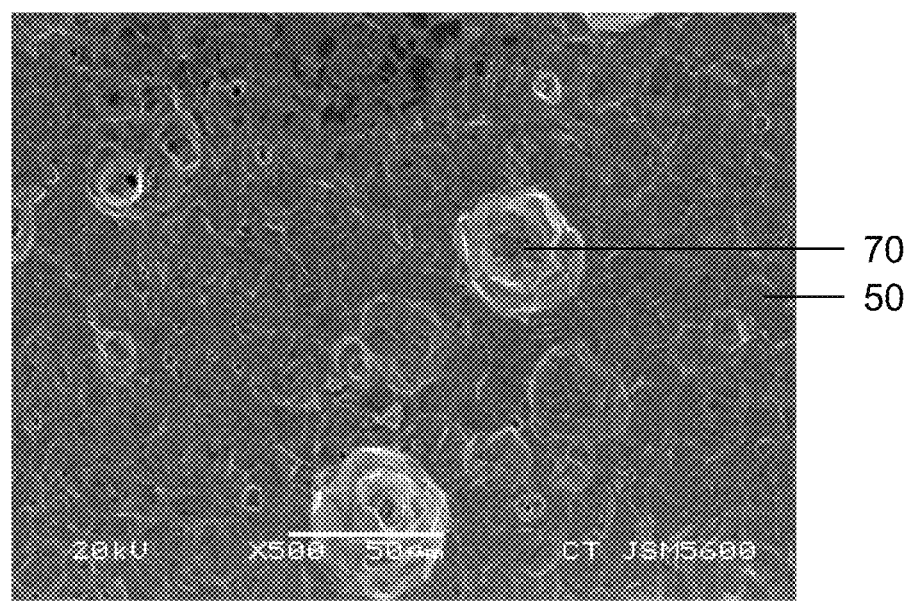

FIGS. 12(e) and 12(f) are SEMs at increased magnifications of the surface morphology of horizontal surface 50 of FIG. 12(a) with etch pits 70 after 4 minutes of etch treatment as described above.

Figure 12G:
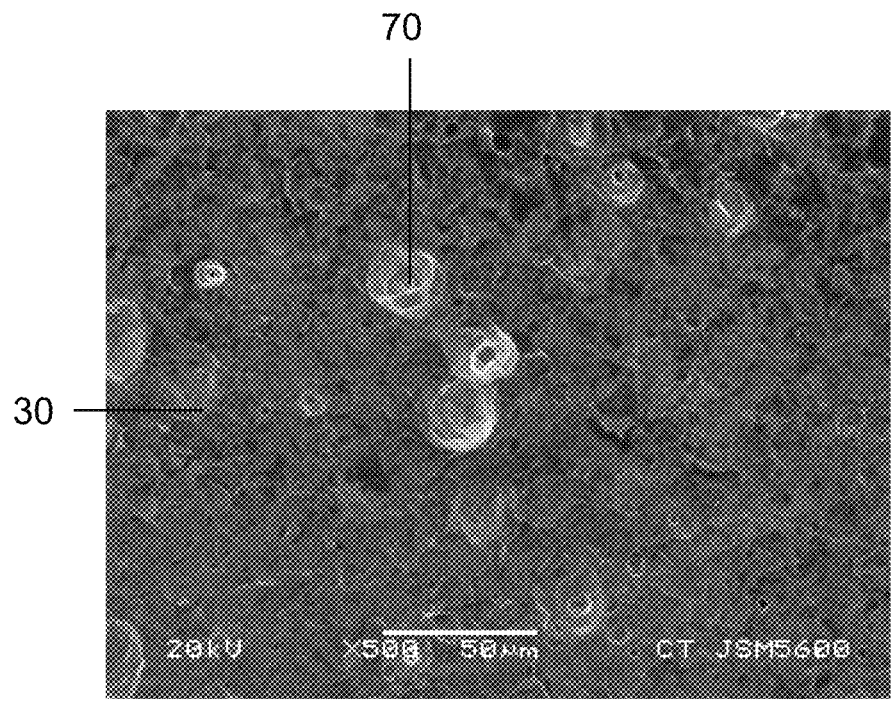
FIGS. 12(g) and 12(h) are SEMS at increased magnifications of the surface morphology of top surface of valve retainer 30 after 4 minutes of etching with 2 vol % HF in 30 vol % HNO$_3$ acid at room temperature with sonication (40 KHz), followed by rinsing and drying.
Figure 12H:
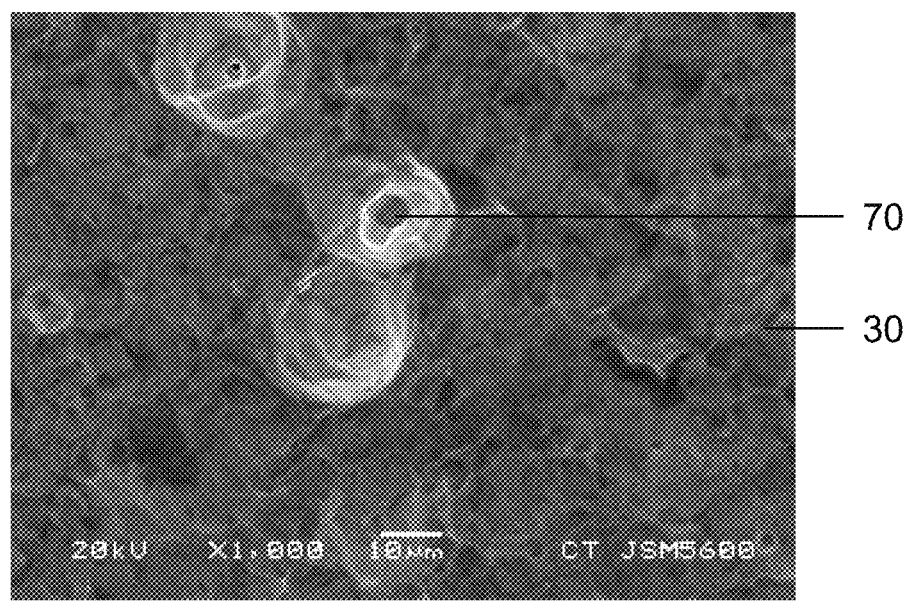

FIGS. 12(g) and 12(h) are SEMS at increased magnifications of the surface morphology of top surface of valve retainer 30 of FIG. 12(a) after 4 minutes of etch treatment as described above.

FIGS. 12(a) through 12(h) show etch pits 70 on all surfaces of valve retainer 10. The etch pits 70 increase in size and number with increased etch duration. When FIG. 12(b) was compared to FIG. 9(b), it was noted that there was significant material loss of inner wall 80 of horizontal surface 50 which suggested that prolonged etching time greater than 4 minutes may not be preferred.

Figure 13A:
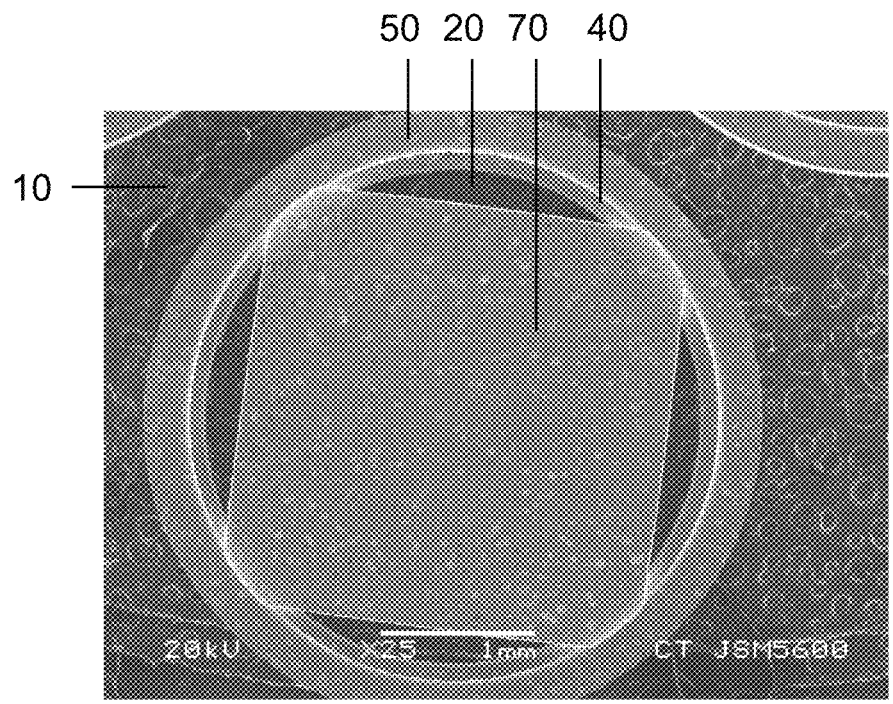
FIG. 13(a) provides an SEM image of valve retainer 10 as exemplified in FIG. 8(a) after 5 minutes of etching with 2 vol % HF in 30 vol % HNO$_3$ acid at room temperature with sonication (40 KHz), followed by rinsing and drying.

FIG. 13(a) provides an SEM image of valve retainer 10 as exemplified in FIG. 8(a) after 5 minutes of etch treatment as described above.

Figure 13B:
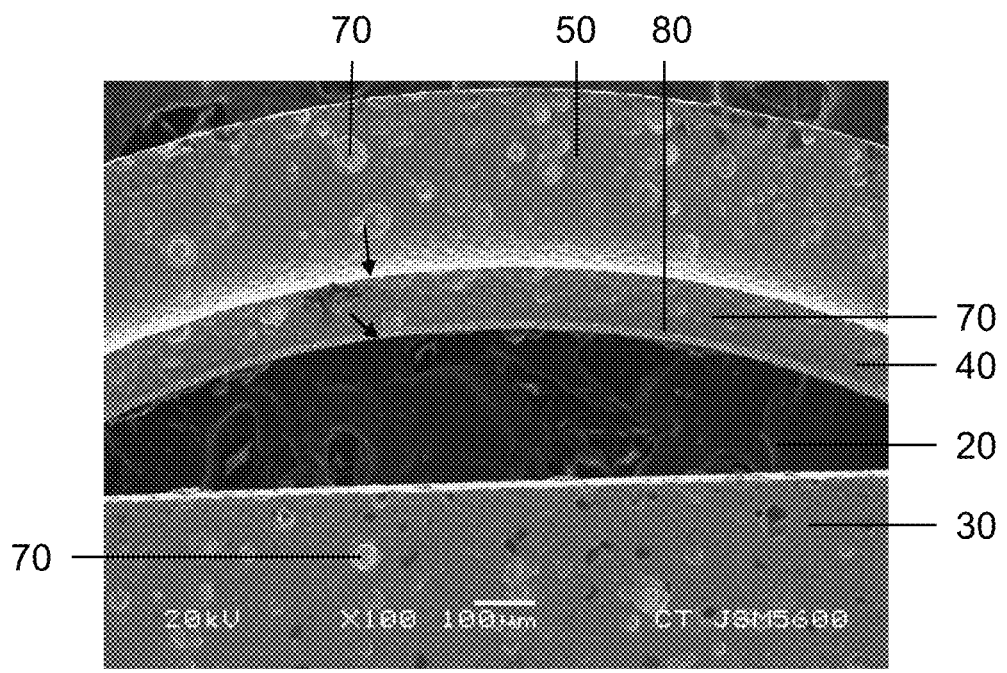
FIGS. 13(b), (c), and (d) are successive higher magnification SEM images after 5 minutes of etching with 2 vol % HF in 30 vol % HNO$_3$ acid at room temperature with sonication (40 KHz), followed by rinsing and drying.

FIGS. 13(b), (c), and (d) are successive higher magnification SEM images of FIG. 13(a) after 5 minutes of etch treatment as described above.

FIG. 13(b) provides a magnified SEM image of FIG. 13(a) showing top surface of valve retainer 30, vertical drug flow channel 20, horizontal WEDM plane without recast layer (roughened surface) and horizontal surface 50 without recast splatter 60 after 5 minutes of etch treatment as described above. Etch pits 70 were noted on the titanium surface. The arrows mark horizontal WEDM plane 40.

Figure 13C:
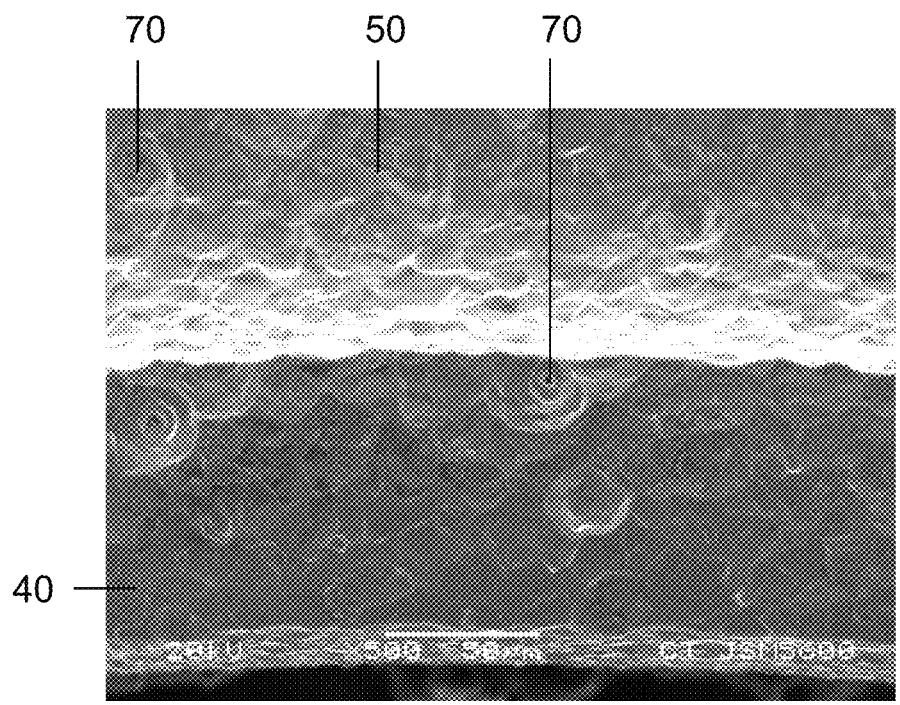
FIG. 13(c) is an SEM of increased magnification of FIG. 13(a) showing horizontal WEDM plane 40 without recast layer and horizontal surface 50 without recast splatter 60 after 5 minutes of etching with 2 vol % HF in 30 vol % HNO$_3$ acid at room temperature with sonication (40 KHz), followed by rinsing and drying. Etch pits 70 in the titanium surface were noted.

FIG. 13(c) is an SEM of increased magnification of FIG. 13(a) showing horizontal WEDM plane 40 without recast layer and horizontal surface 50 without recast splatter 60 after 5 minutes of etch treatment as described above. Etch pits 70 in the titanium surface were noted.

Figure 13D:
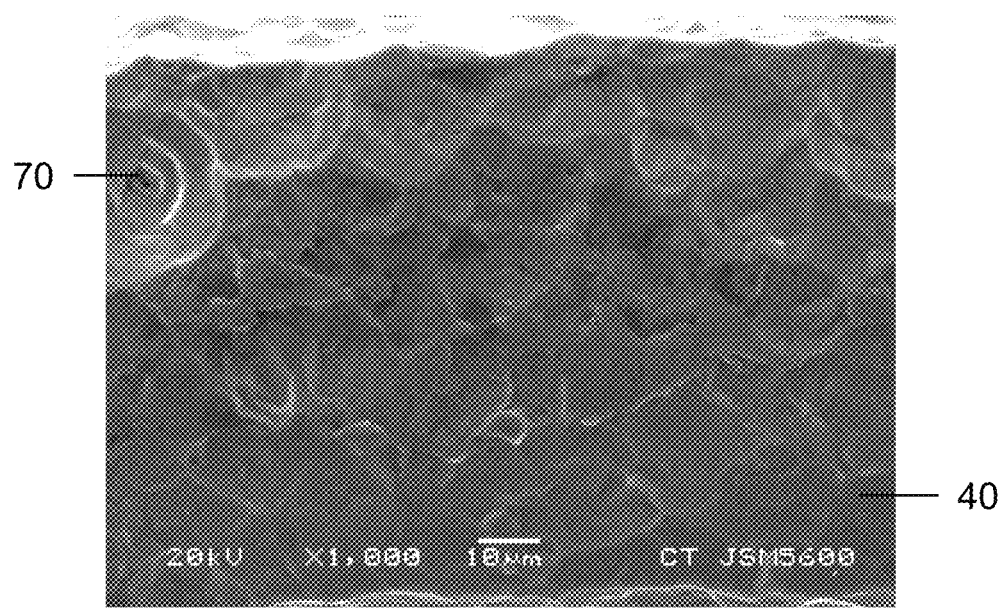
FIG. 13(d) is an SEM of FIG. 13(a) showing horizontal WEDM plane 40 with etch pits 70 after 5 minutes of etching with 2 vol % HF in 30 vol % HNO$_3$ acid at room temperature with sonication (40 KHz), followed by rinsing and drying.

FIG. 13(d) is an SEM of FIG. 13(a) showing horizontal WEDM plane 40 with etch pits 70 after 5 minutes of etch treatment as described above.

Figure 13E:
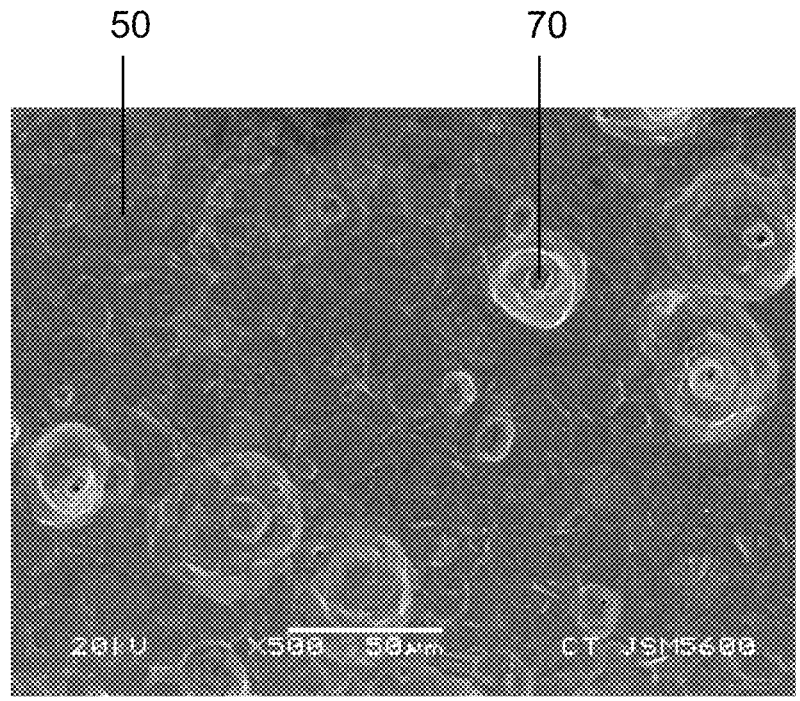
FIGS. 13(e) and 13(f) are SEMs at increased magnifications of the surface morphology of horizontal surface 50 with etch pits 70 after 5 minutes of etching with 2 vol % HF in 30 vol % HNO$_3$ acid at room temperature with sonication (40 KHz), followed by rinsing and drying.
Figure 13F:
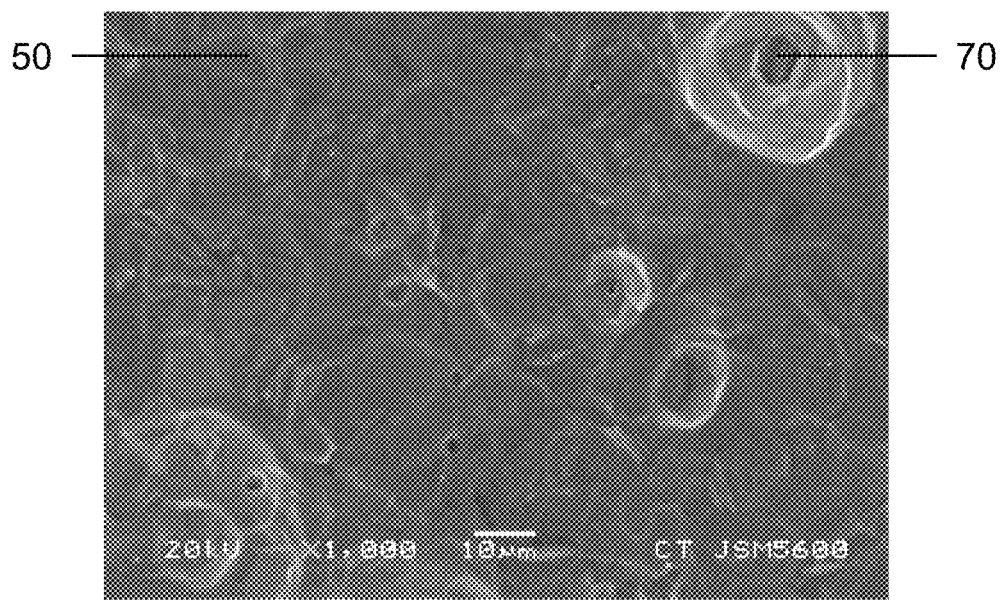

FIGS. 13(e) and 13(f) are SEMs at increased magnifications of the surface morphology of horizontal surface 50 of FIG. 13(a) with etch pits 70 after 5 minutes of etch treatment as described above.

Figure 13G:
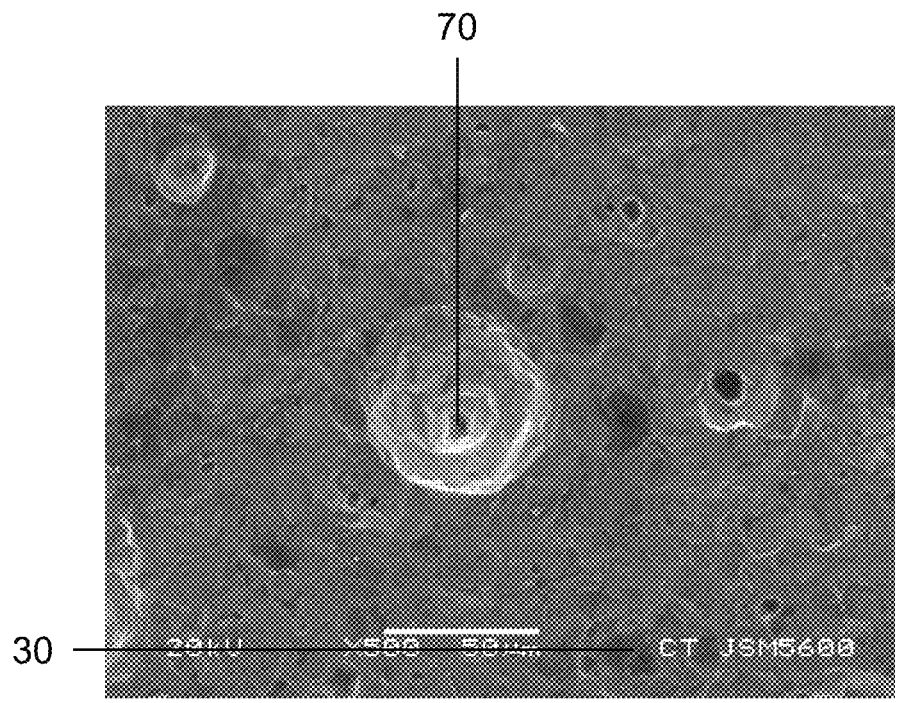
FIGS. 13(g) and 13(h) are SEMS at increased magnifications of the surface morphology of top surface of valve retainer 30 after 5 minutes of etching with 2 vol % HF in 30 vol % HNO$_3$ acid at room temperature with sonication (40 KHz), followed by rinsing and drying. Etch pits 70 are noted.
Figure 13H:
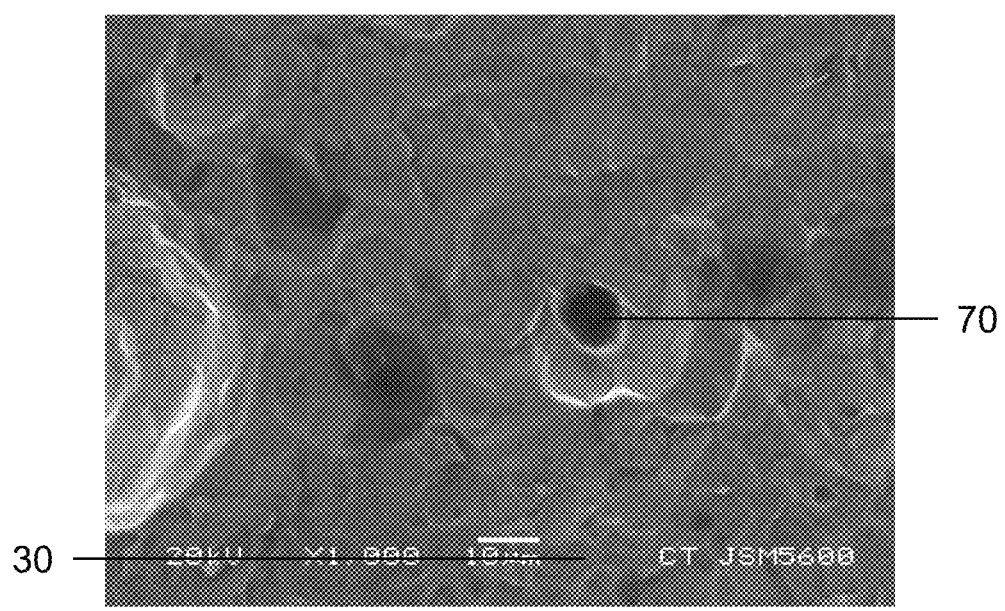

FIGS. 13(g) and 13(h) are SEMS at increased magnifications of the surface morphology of top surface of valve retainer 30 of FIG. 13(a) after 5 minutes of etch treatment as described above.

FIGS. 13(a) through 13(h) show etch pits 70 on all surfaces of valve retainer 10. The etch pits 70 increase in size and number with increased etch duration. When FIG. 13(b) was compared to FIG. 9(b), it was noted that there was significant material loss of inner wall 80 of horizontal surface 50 which suggested that etching times greater than 5 minutes may not be preferred.

Comparison of FIGS. 8(a) through 8(h) with regard to FIGS. 9(a) through 13(h) indicated that an etching process of about 2 minutes or less was sufficient to remove the recast layer and/or splatter without substantially causing etching of the underlying metal substrate.

Energy Dispersive X-ray Spectroscopy (EDS)

EDS spectra were acquired from an as-received control sample (FIG. 14) and five samples etched for 1 minute, 2 minutes, 3 minutes, 4 minutes, and 5 minutes under conditions describe above (FIGS. 15 through 19).

Figure 14:
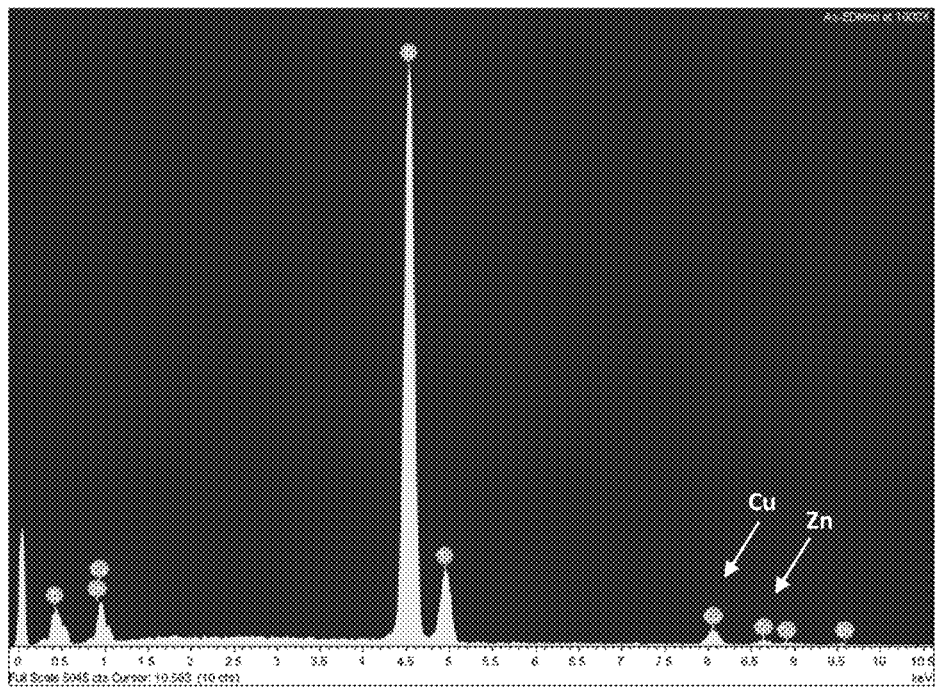
FIG. 14 provides an EDS spectrum showing the presence of Cu and Zn in the recast layer from an as-received WEDM valve retainer 10.

FIG. 14 provides an EDS spectrum showing the presence of Cu and Zn in the recast layer from an as-received WEDM valve retainer 10. The spectrum was acquired from an area viewed by SEM at 1000×. As shown on FIG. 14, the recast layer on as-received WEDM processed valve retainer 10 contained Cu, Zn, and Ti. The recast layer was composed of approximately 8 wt % of copper and approximately 3 wt % of zinc with the balance being Ti.

Figure 15:
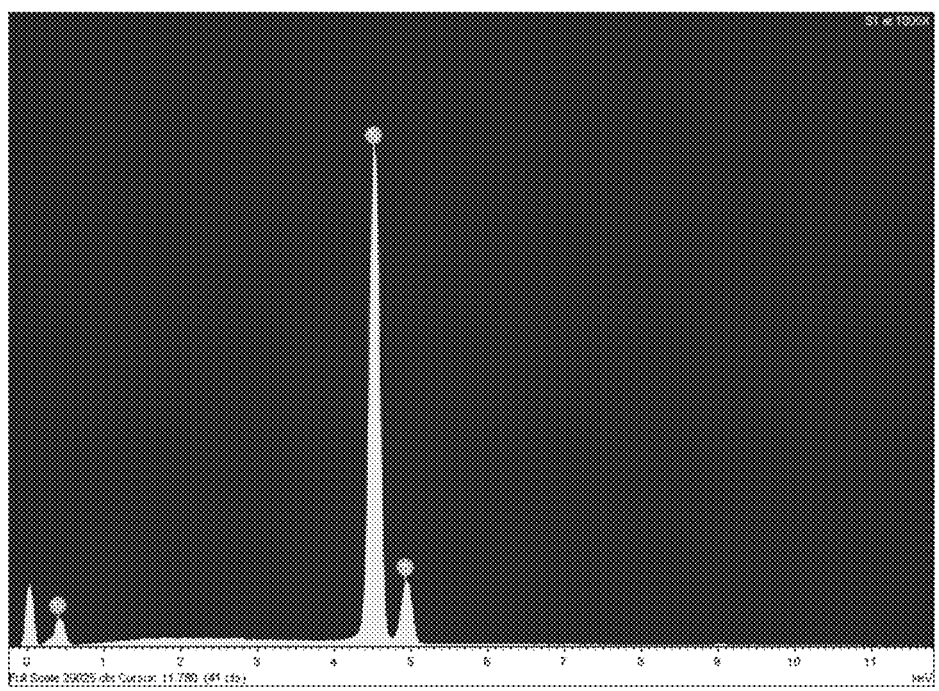
FIG. 15 provides an EDS spectrum showing the absence of Cu and Zn subsequent to WEDM recast layer removal from an as-received WEDM valve retainer 10 after 1 minute of etching in 2 vol % HF in 30 vol % HNO$_3$ acid at room temperature with sonication (40 KHz), followed by rinsing and drying.

FIG. 15 provides an EDS spectrum showing the absence of Cu and Zn subsequent to WEDM recast layer removal after 1 minute of etch treatment as described above.

Figure 16:
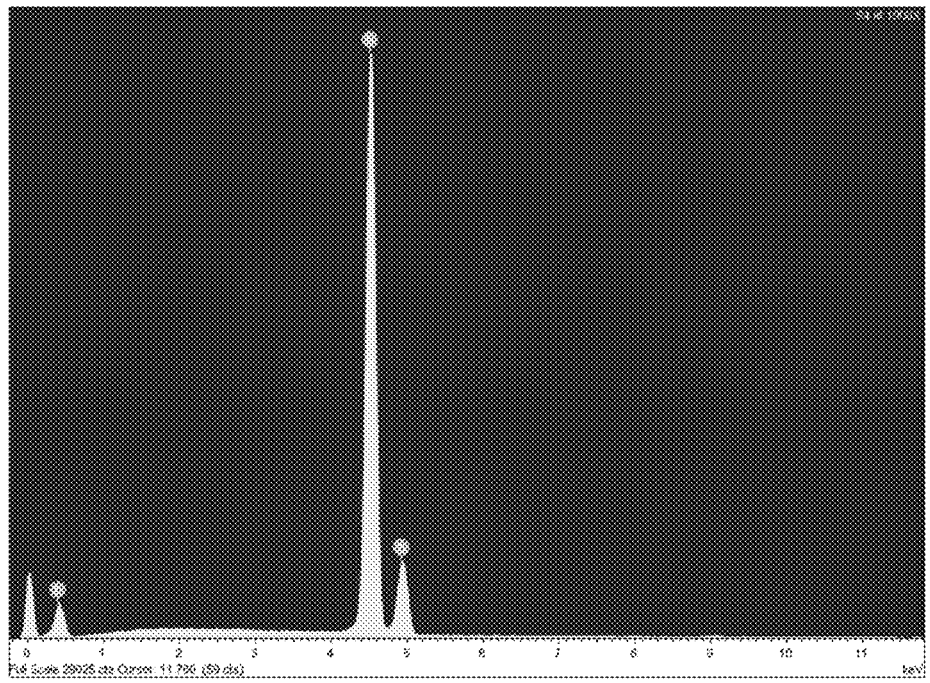
FIG. 16 provides an EDS spectrum showing the absence of Cu and Zn subsequent to WEDM recast layer removal from an as-received WEDM valve retainer 10 after 2 minutes of etching in 2 vol % HF in 30 vol % HNO$_3$ acid at room temperature with sonication (40 KHz), followed by rinsing and drying.

FIG. 16 provides an EDS spectrum showing the absence of Cu and Zn subsequent to WEDM recast layer removal after 2 minutes of etch treatment as described above.

Figure 17:
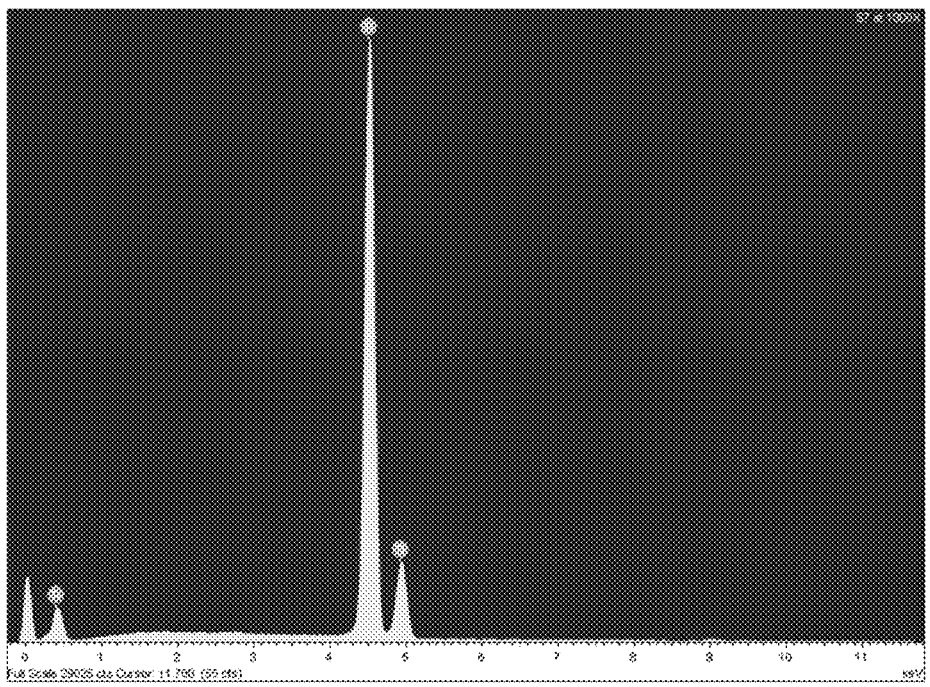
FIG. 17 provides an EDS spectrum showing the absence of Cu and Zn subsequent to WEDM recast layer removal from an as-received WEDM valve retainer 10 after 3 minutes of etching in 2 vol % HF in 30 vol % HNO$_3$ acid at room temperature with sonication (40 KHz), followed by rinsing and drying.

FIG. 17 provides an EDS spectrum showing the absence of Cu and Zn subsequent to WEDM recast layer removal after 3 minutes of etch treatment as described above.

Figure 18:
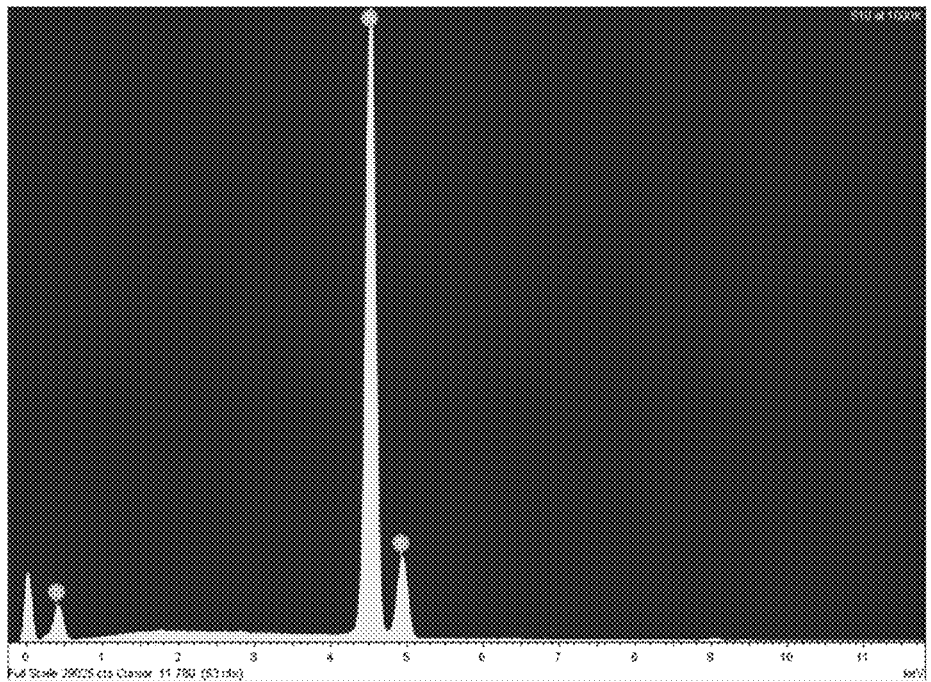
FIG. 18 provides an EDS spectrum showing the absence of Cu and Zn subsequent to WEDM recast layer removal from an as-received WEDM valve retainer 10 after 4 minutes of etching in 2 vol % HF in 30 vol % HNO$_3$ acid at room temperature with sonication (40 KHz), followed by rinsing and drying.

FIG. 18 provides an EDS spectrum showing the absence of Cu and Zn subsequent to WEDM recast layer removal after 4 minutes of etch treatment as described above.

Figure 19:
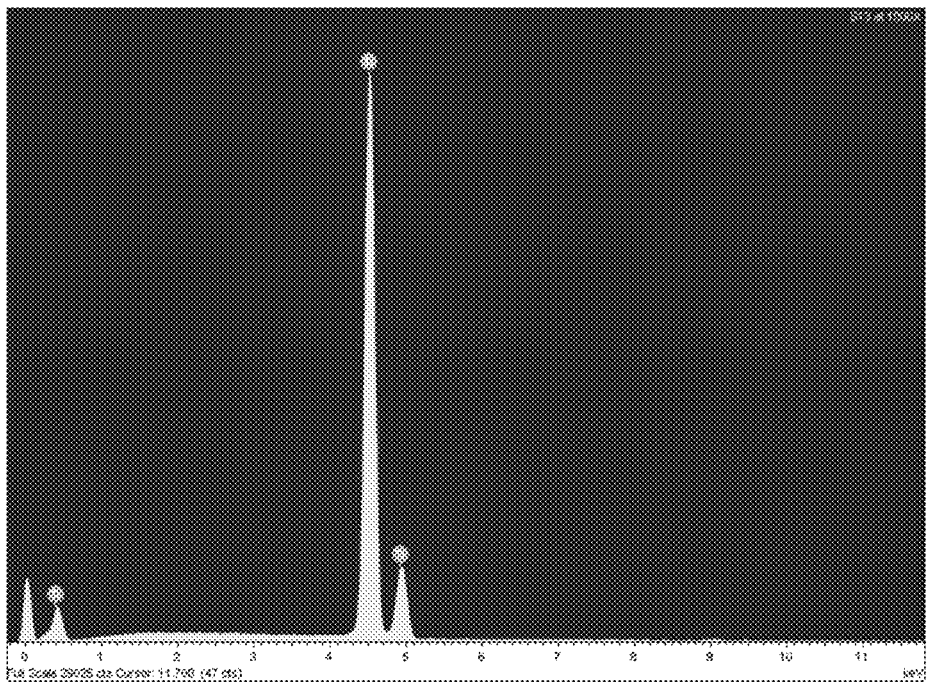
FIG. 19 provides an EDS spectrum showing the absence of Cu and Zn subsequent to WEDM recast layer removal from an as-received WEDM valve retainer 10 after 5 minutes of etching in 2 vol % HF in 30 vol % HNO$_3$ acid at room temperature with sonication (40 KHz), followed by rinsing and drying.

FIG. 19 provides an EDS spectrum showing the absence of Cu and Zn subsequent to WEDM recast layer removal after 5 minutes of etch treatment as described above.

FIGS. 14 through 19 indicated that an etching process of about 2 minutes or less was sufficient to remove the recast layer and/or splatter.

More particularly, FIG. 15 demonstrates that 1 minute etch treatment, as described above, is sufficiently effective in removing the recast layer to the extent that Cu and Zn are no longer detected by EDS. This is in good agreement with the SEM images in FIG. 9 where the WEDM recast layer appears to be completely removed after 1 minute etching under identical conditions. No Cu or Zn was detected in samples etched for periods of time longer than 1 minute.

Material Removal Rate

A quadratic relationship was established based on dimensional measurements taken before and after the etch treatment as described above.

Figure 20:
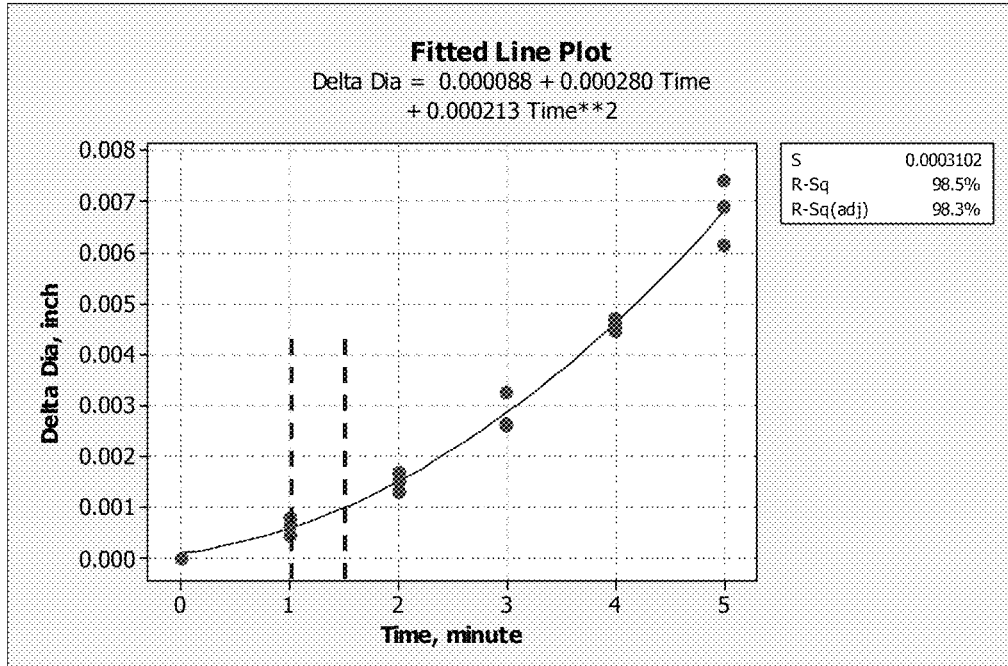
FIG. 20 depicts the removal rate of a recast layer based on dimensional changes of the outside diameter of valve retainer 10 after an etch treatment of 2 vol % HF in 30 vol % HNO$_3$ acid at room temperature with sonication (40 KHz), followed by rinsing and drying.

FIG. 20 depicts the removal rate of a recast layer and any underlying material based on dimensional changes of the outside diameter of valve retainer 10 from the etch treatment as described above.

Figure 21:
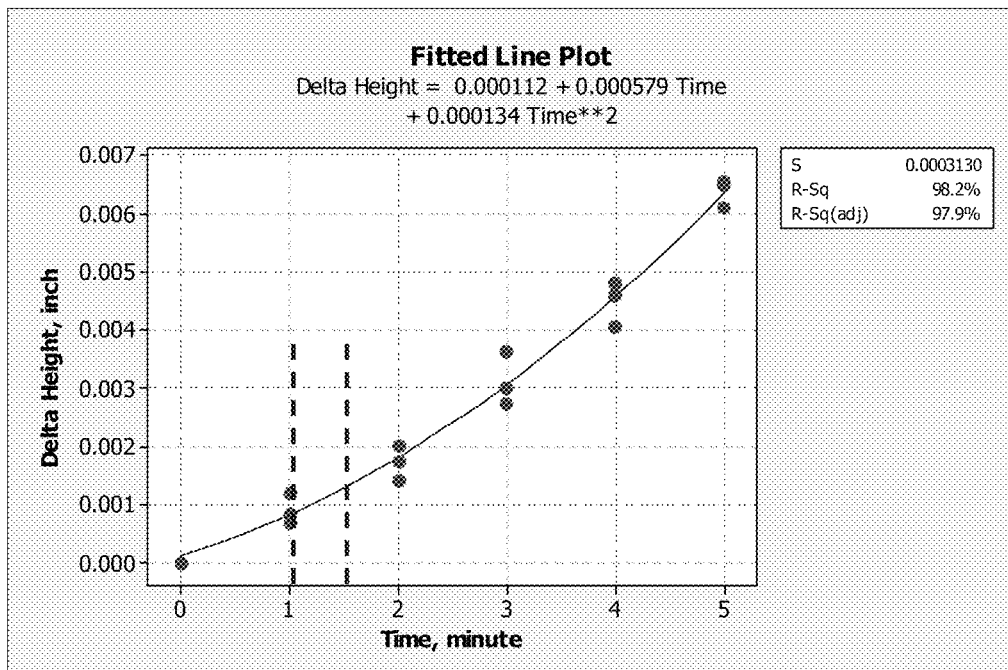
FIG. 21 depicts the removal rate of a recast layer based on dimensional changes in overall length (top to bottom) of valve retainer 10 after an etch treatment of 2 vol % HF in 30 vol % HNO$_3$ acid at room temperature with sonication (40 KHz), followed by rinsing and drying.

FIG. 21 depicts the removal rate of a recast layer and any underlying material based on dimensional changes in overall length (top to bottom) of valve retainer 10 from the etch treatment as described above.

Figure 22:
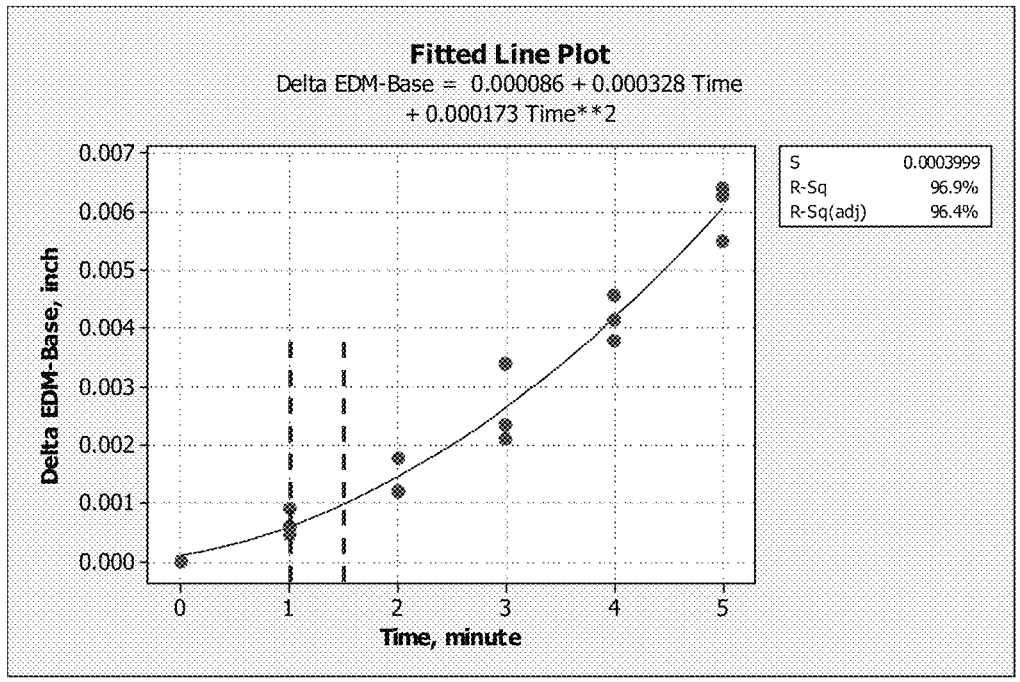
FIG. 22 depicts the removal rate of a recast layer based on dimensional changes measured from horizontal WEDM plane 40 to the bottom of valve retainer 10 after an etch treatment of 2 vol % HF in 30 vol % $HNO_3$ acid at room temperature with sonication (40 KHz), followed by rinsing and drying.

FIG. 22 depicts the removal rate of a recast layer and any underlying material based on dimensional changes measured from horizontal WEDM plane 40 to the bottom of valve retainer 10 from the etch treatment as described above.

Figure 23:
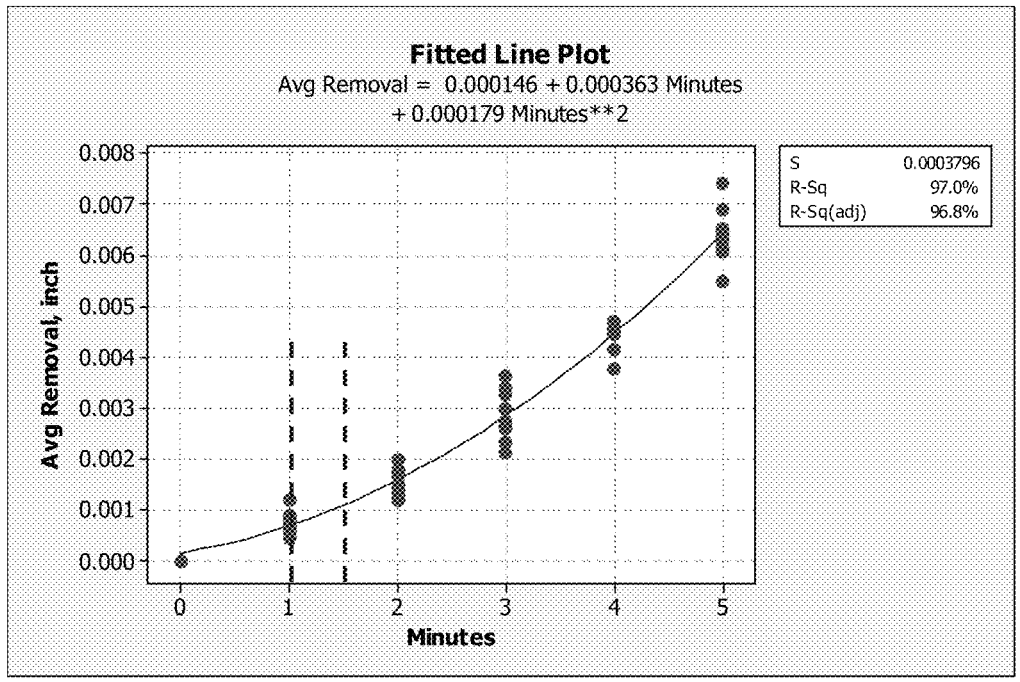
FIG. 23 depicts the average removal rate of a recast layer by combining the dimensional changes of outside diameter overall length, and length from the horizontal WEDM plane 40 to the bottom of valve retainer 10 after an etch treatment of 2 vol % HF in 30 vol % $HNO_3$ acid at room temperature with sonication (40 KHz), followed by rinsing and drying.

FIG. 23 depicts the average removal rate of a recast layer by combining the dimensional changes of outside diameter overall length, and length from the horizontal WEDM plane 40 to the bottom of valve retainer 10 from the etch treatment as described above.

The quadratic model fit the data very well as can be seen in FIGS. 20 through 23. The vertical lines noted on each figure define a time period of 60+/30 seconds. The model could be used in an automated system where the machined parts could be treated for a period of time and removed immediately thereafter.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A process comprising the steps:
providing a wire electric discharge machined (WEDM) part with a copper and zinc recast layer or copper and zinc splatter from the WEDM machining;
contacting the WEDM part with the copper and zinc recast layer or copper and zinc splatter with a treatment solution comprising an aqueous solution of 1-3 volume percent hydrofluoric acid and 20-40 volume percent nitric acid to remove the copper and zinc recast layer or copper and zinc splatter, providing a treated WEDM part devoid of a copper and zinc recast layer or copper and zinc splatter;
wherein the copper and zinc recast layer or splatter is removed from the underlying part surface, wherein pitting of the surface is 3 or less pits per 200 square microns, wherein the WEDM part comprises one of titanium, molybdenum, niobium, zirconium, tantalum, aluminum, vanadium or mixtures thereof, and wherein the recast layer further comprises one of the corresponding titanium, molybdenum, niobium, zirconium, tantalum, aluminum, vanadium or mixtures thereof from the WEDM part.

2. The process of claim 1, further comprising the step:
rinsing the treated WEDM part with a rinse solvent to provide a finished machined part.

3. The process of claim 1, wherein the treatment solution is maintained at a temperature between about 10° C. and 60° C.

4. The process of claim 1, wherein the treatment period from about 30 to about 180 seconds.

5. The process of claim 1, wherein the contacting step further includes sonication.

6. The process of claim 1, wherein the metal is a titanium alloy.

7. The process of claim 1, wherein a quadratic relationship is established between copper and zinc recast layer or copper and zinc splatter removal and processing time, wherein $L=0.000146+0.000363\,T+0.000179\,T^2$, where L is the copper and zinc recast layer or copper and zinc splatter layer in inches and T is time in minutes.

8. A process comprising the steps:
providing a machined part with a copper and zinc recast layer, burr or splatter from machining;
contacting the machined part with a treatment solution comprising an aqueous solution of 1-3 volume percent hydrofluoric acid and 20-40 volume percent nitric acid to remove the copper and zinc recast layer, burr or splatter, providing a treated machined part devoid of a copper and zinc recast layer, burr or splatter;
wherein the copper and zinc recast layer or splatter is removed from the underlying part surface, wherein pitting of the surface is 3 or less pits per 200 square microns, and wherein the WEDM part comprises one of titanium, molybdenum, niobium, zirconium, tantalum, aluminum, vanadium or mixtures thereof, and wherein the recast layer further comprises one of the corresponding titanium, molybdenum, niobium, zirconium, tantalum, aluminum, vanadium or mixtures thereof from the WEDM part.

9. The process of claim 8, further comprising the step:
rinsing the treated machined part with a rinse solvent to provide a finished machined part.

10. The process of claim 8, wherein the treatment solution is maintained at a temperature between about 10° C. and 60° C.

11. The process of claim 8, wherein the treatment period is from about 30 to about 180 seconds.

12. The process of claim 8, wherein the contacting step further includes sonication.

13. The process of claim 8, wherein the metal is a titanium alloy.

14. The process of claim 8, wherein a quadratic relationship is established between copper and zinc recast layer, burr or splatter removal and processing time, wherein $L=0.000146+0.000363\,T+0.000179\,T^2$, where L is a copper and zinc recast layer, burr or splatter layer in inches and T is time in minutes.

15. The process of claim 8, wherein from about 10 to about 100 microns of the copper and zinc recast layer, splatter or burr surface is removed.

* * * * *